United States Patent
Engel et al.

(10) Patent No.: US 6,432,881 B1
(45) Date of Patent: *Aug. 13, 2002

(54) 2-BENZOYLCYCLOHEXANE-1,3-DIONE AS HERBICIDES

(75) Inventors: Stefan Engel, Wörrstadt; Joachim Rheinheimer, Ludwigshafen; Ernst Baumann, Dudenhofen; Wolfgang von Deyn, Neustadt; Regina Luise Hill, Speyer; Guido Mayer; Ulf Misslitz, both of Neustadt; Oliver Wagner, Ludwigshafen; Matthias Witschel, Ludwigshafen; Martina Otten, Ludwigshafen; Helmut Walter, Obrigheim; Karl-Otto Westphalen, Speyer, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 25 days.

(21) Appl. No.: 09/485,231
(22) PCT Filed: Aug. 5, 1998
(86) PCT No.: PCT/EP98/04634
§ 371 (c)(1),
(2), (4) Date: Feb. 7, 2000
(87) PCT Pub. No.: WO99/10327
PCT Pub. Date: Mar. 4, 1999

(30) Foreign Application Priority Data

Aug. 7, 1997 (DE) .......................... 197 34 164

(51) Int. Cl.$^7$ .................... C07D 231/12; C07D 231/14; A01N 43/56
(52) U.S. Cl. .................. 504/280; 504/282; 504/287; 548/366.1; 548/374.1; 548/564; 548/363
(58) Field of Search ............... 548/564, 563, 548/366.1, 374.1; 504/287, 280, 282

(56) References Cited

U.S. PATENT DOCUMENTS

| | | | |
|---|---|---|---|
| 4,938,796 A | 7/1990 | Buren et al. | 71/98 |
| 4,943,310 A | 7/1990 | Angermann | 71/88 |
| 5,250,501 A | 10/1993 | Barton et al. | 504/266 |
| 5,426,091 A | 6/1995 | Barton et al. | 504/279 |
| 5,563,115 A | 10/1996 | Barton et al. | 504/288 |
| 5,834,404 A | 11/1998 | Sagae et al. | 504/348 |

FOREIGN PATENT DOCUMENTS

| | | |
|---|---|---|
| EP | 278 742 | 8/1988 |
| EP | 298 680 | 1/1989 |

OTHER PUBLICATIONS

Patent Abst of Jp 06321932.
Patent Abst of Jp 06271562.

Primary Examiner—Richard L. Raymond
Assistant Examiner—Hong Liu
(74) Attorney, Agent, or Firm—Keil & Weinkauf

(57) ABSTRACT

2-Benzoylcyclohexane-1,3-diones of formula I :

where:

$R^1$ and $R^2$ are each hydrogen, mercapto, nitro, halogen, cyano, thiocyanato, alkyl, haloalkyl, alkoxy, alkenyl, alkynyl, —$OR^3$, —$OCOR^3$, —$OSO_2R^3$, —$S(O)_nR^3$ (n=0, 1, 2), —$SO_2OR^3$, —$SO_2N(R^3)_2$, —$NR^3SO_2R^3$ or —$NR^3COR^3$;

$R^3$ is hydrogen or optionally substituted alkyl, haloalkyl, alkenyl, alkynyl, phenyl or phenylalkyl;

Q is optionally substituted cyclohexane-2-yl-1,3-dione;

$X^1$ is optionally substituted alkylene, propenylene, alkenylene or alkynylene;

$R^4$ is hydrogen or optionally substituted alkyl, alkenyl, alkynyl, phenyl, phenylalkyl;

Het is a three- to six-membered, optionally substituted heterocyclic or heteroaromatic group;

and agriculturally useful salts thereof, processes and intermediates for preparing compounds of formula I, compositions comprising them, and the use of the compounds of formula I and the compositions comprising them for controlling harmful plants are described.

20 Claims, No Drawings

2-BENZOYLCYCLOHEXANE-1,3-DIONE AS HERBICIDES

The present invention relates to substituted 2-benzoylcyclohexane-1,3-diones of the formula I:

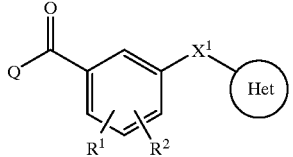

where:
- $R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl, —$OR^3$, —$OCOR^3$, —$OSO_2R^3$, —$S(O)_nR^3$, —$SO_2OR^3$, —$SO_2N(R^3)_2$, —$NR^3SO_2R^3$ or —$NR^3COR^3$;
- $R^3$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl; where the abovementioned alkyl radicals may be partially or fully halogenated and/or may carry one to three of the following groups:
  hydroxyl, mercapto, amino, cyano, $R^3$, —$OR^3$, —$SR^3$, —$N(R^3)_2$, =$NOR^3$, —$OCOR^3$, —$SCOR^3$, —$NR^3COR^3$, —$CO_2R^3$, —$COSR^3$, —$CON(R^3)_2$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the eight last mentioned radicals may in turn be substituted;
- n is 0, 1 or 2;
- Q is a cyclohexane-1,3-dione ring with or without substitution which is attached in position 2;
- $X^1$ is a straight-chain or branched $C_1$–$C_6$-alkylene, a $C_2$–$C_6$-alkenylene or a $C_2$–$C_6$-alkynylene chain which is interrupted by a hetero atom selected from the group consisting of:
  oxygen or sulfur,
  where the abovementioned alkyl, alkenyl or alkynyl radicals may be partially halogenated and/or may carry one to three of the following groups:
  —$OR^4$, —$OCOR^4$, —$OCONHR^4$ or —$OSO_2R^4$;
- is hydrogen, $C_1$–$C_6$-alkyl, $C_2$–$C_6$-alkenyl, $C_2$–$C_6$-alkynyl, phenyl, phenyl-$C_1$–$C_6$-alkyl, where the abovementioned alkyl, alkenyl or alkynyl radicals may be partially or fully halogenated and/or may be substituted by one or more of the following radicals:
  hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;
- Het is a three- to six-membered partially or fully saturated heterocyclic group or a three- to six-membered heteroaromatic group having up to three hetero atoms selected from the following three groups:
  nitrogen,
  oxygen in combination with at least one nitrogen or
  sulfur in combination with at least one nitrogen,
  where the abovementioned heterocyclic or heteroaromatic group may be partially or fully halogenated and/or may be substituted by $R^5$;
- $R^5$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where the alkyl radicals may in each case be substituted by in each case one or more of the following radicals:
  cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

and agriculturally useful salts thereof.

In addition, the invention relates to processes and intermediates for preparing compounds of the formula I, to compositions comprising them and to the use of the compounds of the formula I and to compositions comprising them for controlling harmful plants.

2-Benzoylcyclohexane-1,3-diones are disclosed in the literature, for example in EP-A 278 742, EP-A 298 680, EP-A 320 864 and WO 96/14285.

However, the herbicidal properties of the prior art compounds and their crop plant safety are not entirely satisfactory.

It is an object of the present invention to provide novel, in particular herbicidally active, compounds having improved properties.

We have found that this object is achieved by the 2-benzoylcyclohexane-1,3-diones of the formula I and their herbicidal activity.

Furthermore, we have found herbicidal compositions which comprise the compounds I and have very good herbicidal activity. Moreover, we have found processes for preparing these compositions and methods for controlling unwanted vegetation using the compounds I.

The present invention also provides stereoisomers of the compounds of the formula I. Pure stereoisomers and also mixtures thereof are included.

Depending on the substitution pattern, the compounds of the formula I may contain one or more chiral centers and, if this is the case, are present as mixtures of enantiomers or diastereomers. The invention provides the pure enantiomers or diastereomers and also mixtures thereof.

The compounds of the formula I may also be present in the form of their agriculturally useful salts, the kind of salt generally not being important. The salts of those cations or the acid addition salts of those acids whose cations or anions, respectively, do not adversely affect the herbicidal activity of the compounds I are generally suitable.

Suitable cations are in particular ions of the alkali metals, preferably lithium, sodium and potassium, of the alkaline earth metals, preferably calcium and magnesium, and of the transition metals, preferably manganese, copper, zinc and iron, and ammonium, where, if desired, one to four hydrogen atoms may be replaced by $C_1$–$C_4$-alkyl or hydroxy-$C_1$–$C_4$-alkyl and/or one phenyl or benzyl, preferably diisopropylammonium, tetramethylammonium, tetrabutylammonium, trimethylbenzylammonium, furthermore phosphonium ions, sulfonium ions, preferably tri($C_1$–$C_4$-alkyl)sulfonium, and sulfoxonium ions, preferably tri($C_1$–$C_4$-alkyl)sulfoxonium.

Anions of usable acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and the anions of $C_1$–$C_4$-alkanoic acids, preferably formate, acetate, propionate and butyrate.

Emphasis is given to the compounds of the formula I according to the invention where the variable Q is a cyclohexane-1,3-dione ring of the formula II

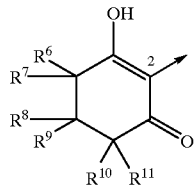

which is attached in position 2, where II may also represent the tautomeric formulae II' and II",

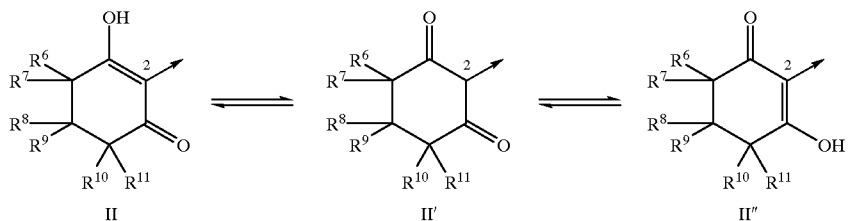

where

R$^6$, R$^7$, R$^9$ and R$^{11}$ are each hydrogen or C$_1$–C$_4$-alkyl;

R$^8$ is hydrogen, C$_1$–C$_4$-alkyl or C$_3$–C$_4$-cycloalkyl, where the two last mentioned groups may carry one to three of the following substituents:
halogen, C$_1$–C$_4$-alkylthio or C$_1$–C$_4$-alkoxy; or
is tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the 6 last mentioned radicals may be substituted by one to three C$_1$–C$_4$-alkyl radicals;

R$^{10}$ is hydrogen, C$_1$–C$_4$-alkyl or C$_1$–C$_6$-alkoxycarbonyl; or

R$^8$ and R$^{11}$ together form a π bond or a three- to six-membered carbocyclic ring; or the CR$^8$R$^9$ unit may be replaced by C=O.

Process A

Reactions of the cyclohexane-1,3-dione of the formula II with an activated carboxylic acid IIIa or a carboxylic acid IIIb, which is preferably activated in situ, to give the acylation product IV, and subsequent rearrangement to the compounds of the formula I according to the invention.

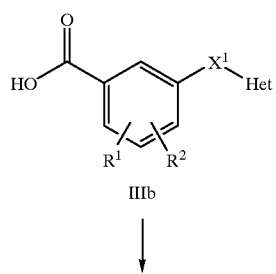

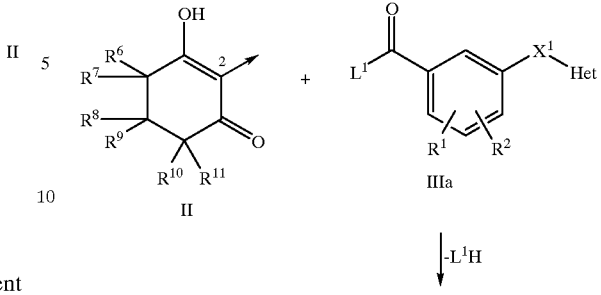

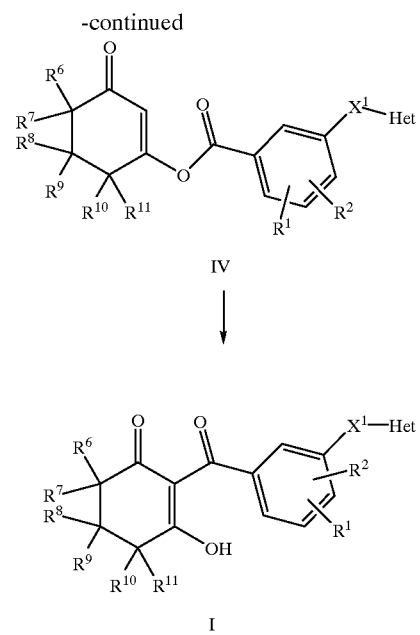

L$^1$ is a nucleophilically replaceable leaving group such as halogen, for example bromine or chlorine, hetaryl, for example imidazolyl or pyridyl, or carboxylate, for example acetate, trifluoroacetate, etc.

The activated carboxylic acid can be employed directly, as in the case of acyl halides, or be generated in situ, for example by using dicyclohexylcarbodiimide, triphenylphosphine/azodicarboxylic esters, 2-pyridine disulfid/triphenylphosphine, carbonyldiimidazole, etc.

It may be advantageous to carry out the acylation reaction in the presence of a base. Starting materials and auxiliary base are advantageously employed in equimolar amounts. A slight excess of auxiliary base, for example 1.2 to 1.5 molar equivalents, based on II, may be advantageous under certain circumstances.

Suitable auxiliary bases are tertiary alkylamines, pyridine or alkali metal carbonates. Examples of solvents which can be used are chlorinated hydrocarbons, such as methylene chloride, 1,2-dichloroethane, aromatic hydrocarbons, such as toluene, xylene, chlorobenzene, ethers, such as diethyl ether, methyl tert-butyl ether, tetrahydrofuran, dioxane, polar aprotic solvents, such as acetonitrile, dimethylformamide, dimethyl sulfoxide, or esters such as ethyl acetate, or mixtures of these.

If acyl halides are employed as activated carboxylic acid component, it may be advantageous to cool the reaction mixture to 0–10° C. when adding this reaction partner. The mixture is subsequently stirred at 20–100° C., preferably at 25–50° C., until the reaction is complete. Work-up is carried out in a customary manner, for example by pouring the reaction mixture into water and extracting the product of value. Solvents which are particularly suitable for this purpose are methylene chloride, diethyl ether and ethyl acetate. After the organic phase has been dried and the solvent has been removed, the crude enol ester of the formula IV is purified, preferably by chromatography. Alternatively, it is possible to employ the crude enol ester of the formula IV without further purification for the rearrangement reaction.

The rearrangement of the enol esters of the formula IV to the compounds of the formula I is advantageously carried out at from 20 to 40° C. in a solvent and in the presence of a base and, if appropriate, in the presence of a cyano compound.

Examples of solvents which can be used are acetonitrile, methylene chloride, 1,2-dichloroethane, dioxane, ethyl acetate, toluene or mixtures of these. Preferred solvents are acetonitrile and dioxane.

Suitable bases are tertiary amines such as triethylamine, pyridine or alkali metal carbonates such as sodium carbonate, potassium carbonate, which are preferably employed in equimolar amounts or up to a four-fold excess, based on the ester. Preference is given to using triethylamine or alkali metal carbonates.

Suitable cyano compounds are inorganic cyanides such as sodium cyanide, potassium cyanide and organic cyano compounds such as acetone cyanohydrin, trimethylsilyl cyanide. They are employed in an amount of 1 to 50 mol percent, based on the ester. Preference is given to using acetone cyanohydrin or trimethylsilyl cyanide, for example in an amount of 5 to 15, preferably 10, mol percent, based on the ester.

Particular preference is given to employing alkali metal carbonates, such as potassium carbonate, in acetonitrile or dioxane.

Work-up can be carried out in a manner known per se. For example, the reaction mixture is acidified with dilute mineral acid, such as 5% strength hydrochloric acid or sulfuric acid, and extracted with an organic solvent, for example methylene chloride, ethyl acetate. The organic phase can be extracted with 5–10% strength alkali metal carbonate solution, for example sodium carbonate or potassium carbonate solution. The aqueous phase is acidified, and the precipitate which forms is filtered off with suction and/or extracted with methylene chloride or ethyl acetate, dried and concentrated.

The benzoic acids of the formula III are novel,

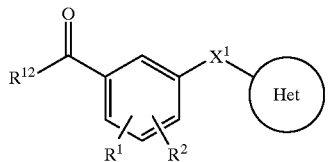

where:
R$^1$ and R$^2$ are each hydrogen, mercapto, nitro, halogen, cyano, thiocyanato, C$_1$–C$_6$-alkyl, C$_1$–C$_6$-haloalkyl, C$_1$–C$_6$-alkoxy, C$_2$–C$_6$-alkenyl, C$_2$–C$_6$-alkynyl, —OR$^3$, —OCOR$^3$, —OSO$_2$R$^3$, S(O)$_n$R$^3$, —SO$_2$OR$^3$, —SO$_2$N(R$^3$)$_2$, —NR$^3$SO$_2$R$^3$ or —NR$^3$COR$^3$;

R$^3$ is hydrogen, C$_1$–C$_6$-alkyl, C$_1$–C$_6$-haloalkyl, C$_2$–C$_6$-alkenyl, C$_2$–C$_6$-alkynyl, phenyl or phenyl-C$_1$–C$_6$-alkyl; where the abovementioned alkyl radicals may be partially or fully halogenated and/or may carry one to three of the following groups:
hydroxyl, mercapto, amino, cyano, R$^3$, —OR$^3$, —SR$^3$, —N(R$^3$)$_2$, =NOR$^3$, —OCOR$^3$, —SCOR$^3$, —NR$^3$COR$^3$, —CO$_2$R$^3$, —COSR$^3$, —CON(R$^3$)$_2$, C$_1$–C$_4$-alkyliminooxy, C$_1$–C$_4$-alkoxyamino, C$_1$–C$_4$-alkylcarbonyl, C$_1$–C$_4$-alkoxy-C$_2$–C$_6$-alkoxycarbonyl, C$_1$–C$_4$-alkylsulfonyl, heterocyclyl, heterocyclyloxy, phenyl, benzyl, hetaryl, phenoxy, benzyloxy and hetaryloxy, where the eight last mentioned radicals may in turn be substituted;

is 0, 1 or 2;

X$^1$ is a straight-chain or branched C$_1$–C$_6$-alkylene, a C$_2$–C$_6$-alkenylene or a C$_2$–C$_6$-alkynylene chain which is interrupted by a hetero atom selected from the group consisting of:
oxygen or sulfur,
where the abovementioned alkyl, alkenyl or alkynyl radicals may be partially halogenated and/or may carry one to three of the following groups:
—OR$^4$, —OCOR$^4$, —OCONHR$^4$ or —OSO$_2$R$^4$;

R$^4$ is hydrogen, C$_1$–C$_6$-alkyl, C$_2$–C$_6$-alkenyl, C$_2$–C$_6$-alkynyl, phenyl, phenyl-C$_1$–C$_6$-alkyl, where the abovementioned alkyl, alkenyl or alkynyl radicals may be partially or fully halogenated and/or may be substituted by one or more of the following radicals:
hydroxyl, mercapto, amino, cyano, nitro, formyl, C$_1$–C$_4$-alkylamino, C$_1$–C$_4$-dialkylamino, C$_1$–C$_4$-alkoxycarbonyl, C$_1$–C$_4$-alkylcarbonyl, C$_1$–C$_4$-alkylcarbonyloxy, C$_1$–C$_4$-alkyl, C$_1$–C$_4$-haloalkyl, C$_1$–C$_4$-alkylthio, C$_1$–C$_4$-haloalkylthio, C$_1$–C$_4$-alkoxy, C$_1$–C$_4$-haloalkoxy;

Het is a three- to six-membered partially or fully saturated heterocyclic group or a three- to six-membered heteroaromatic group having up to three hetero atoms selected from the group consisting of:
nitrogen, oxygen or
sulfur,
where the abovementioned heterocyclic or heteroaromatic group may be partially or fully halogenated and/or may be substituted by R$^5$;

R$^5$ is hydrogen, hydroxyl, mercapto, amino, cyano, nitro, formyl, C$_1$–C$_4$-alkylamino, C$_1$–C$_4$-dialkylamino, C$_1$–C$_4$-alkoxycarbonyl, C$_1$–C$_4$-alkylcarbonyl, C$_1$–C$_4$-alkylcarbonyloxy, C$_1$–C$_4$-alkyl, C$_1$–C$_4$-haloalkyl, C$_1$–C$_4$-alkylthio, C$_1$–C$_4$-haloalkylthio, C$_1$–C$_4$-alkoxy, $C_1$–$C_4$-haloalkoxy, where the alkyl radicals may in each case be substituted by in each case one or more of the following radicals:

cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

$R^{12}$ is hydroxyl or a hydrolyzable radical.

Examples of hydrolyzable radicals are alkoxy, phenoxy, alkylthio and phenylthio radicals which possibly are substituted, halides, hetaryl radicals which are bonded via nitrogen, amino and imino radicals which possibly are substituted, etc.

Preference is given to benzoyl halides IIIa where $L^1$=halogen (= III where $R^{12}$=halogen), IIIa where $R_1$, $R_2$, X and Het are each defined under formula III and $L^1$ is halogen, in particular chlorine or bromine.

Preference is also given to benzoic acids of the formula IIIb (= III where $R^{12}$=hydroxyl), IIIb where $R^1$, $R^2$, $X^1$ and Het are each as defined under formula III.

Preference is also given to benzoic esters of the formula IIIc (=III where $R^{12}$=$C_1$–$C_6$-alkoxy), IIIc where $R^1$, $R^2$, $X^1$ and Het are each as defined under formula III and M is $C_1$–$C_6$-alkoxy.

With regard to the preferred benzoic acids of the formula III, the remarks made under the 2-benzoylcyclohexan-1,3-dione of the formula I apply to the radicals $R^1$, $R^2$, $X^1$ and Het.

The compounds of the formula IIIa (where $L^1$=halogen) can be synthesized by methods similar to those known from the literature (cf. L. G. Fieser, M. Fieser "Reagents for organic Synthesis", Vol. I, pp. 767–769 (1967)) by reacting benzoic acids of the formula IIIb with halogenating agents such as thionyl chloride, thionyl bromide, phosgene, diphosgene, triphosgene, oxalyl chloride and oxalyl bromide.

The benzoic acids of the formula IIIb can be obtained, inter alia, by hydrolyzing the benzoic esters of the formula IIIc (where M=$C_1$–$C_6$-alkoxy).

The benzoic esters of the formula IIIc according to the invention are preparable by various methods known from the literature (for example a: G. Dittus in Houben-Weyl, Methoden der Organischen Chemie, Volume VI/3, Oxygen compounds I, 4th edition, p. 493 ff., Georg Thieme Verlag, 1965; b: T. L. Gilchrist, Heterocyclenchemie, 2nd edition, Verlag Chemie, 1995) as illustrated in the examples that follow.

Process B

Substitution of the benzoic esters Va with suitable nucleophiles VI gives the benzoic esters IIIc according to the invention, Va     VI IIIc where M, $R^1$ and $R^2$ are each as defined above, $L^2$ is a suitable nucleophilically replaceable leaving group such as halogen, for example bromine or chlorine, hetaryl, for example imidazolyl or pyridyl, carboxylate, for example acetate or trifluoroacetate, sulfonate, for example mesylate, triflate, etc., $X^2$ is a straight-chain or branched alkylene, an alkenylene or a alkynylene chain having at least one and a maximum of five carbon atoms where the abovementioned alkylene, alkenylene or alkynylene radicals may be partially halogenated and/or may carry one to three of the following groups:

—$OR^4$, —$OCOR^4$, —$OCONHR^4$ or —$OSO_2R^4$ and $X^3$ is a straight-chain or branched alkylene, an alkenylene or an alkynylene chain having a maximum of five carbon atoms where the abovementioned alkylene, alkenylene or alkynylene radicals may be partially halogenated and/or may carry one to three of the following groups:

—$OR^4$, —$OCOR^4$, —$OCONHR^4$ or —$OSO_2R^4$, where $X^2OX^3$ builds up the variable $X^1$.

In general, the starting materials are employed in equimolar amounts. However, it may be advantageous to employ an excess of one or another component.

If appropriate, it may be advantageous to carry out the reaction in the presence of a base. The starting materials and the auxiliary base are advantageously employed in equimolar amounts. In certain cases, an excess of the auxiliary base, for example 1.5 to 3 molar equivalents, based on Va, may be advantageous.

Suitable auxiliary bases are tertiary alkylamines such as triethylamine and pyridine, alkali metal carbonates, for example sodium carbonate and potassium carbonate, and alkali metal hydrides, for example sodium hydride. Preference is given to using triethylamine, pyridine and potassium carbonate.

Examples of suitable solvents are chlorinated hydrocarbons such as methylene chloride and 1,2-dichloroethane, aromatic hydrocarbons, for example toluene, xylene, chlorobenzene, ethers such as diethyl ether, methyl tert-butyl ether, tetrahydrofuran, dioxane, polar aprotic solvents such as acetonitrile, dimethylformamide and dimethyl sulfoxide, or esters such as ethyl acetate, or mixtures of these.

The reaction temperature is generally in the range from 0° C. to the boiling point of the reaction mixture.

Work-up can be carried out in a manner known per se.

Process C

Substitution of appropriately substituted heterocycles VII with benzoic esters Vb gives the benzoic esters IIIc according to the invention,

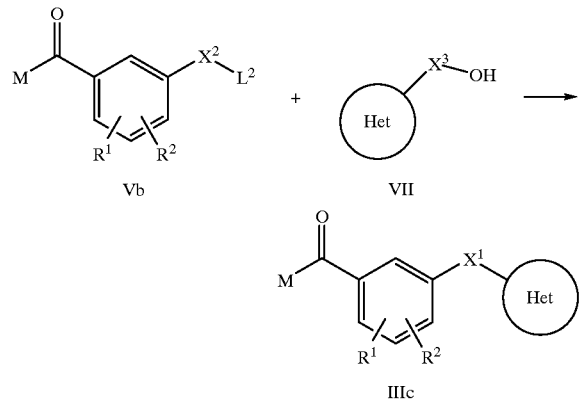

where M, $R^1$ and $R^2$ are each as defined above, $L^2$ is a suitable nucleophilically replaceable leaving group such as halogen, for example bromine or chlorine, hetaryl, for example imidazolyl or pyridyl, carboxylate, for example acetate or trifluoroacetate, sulfonate, for example mesylate, triflate, etc., $X^2$ is a straight-chain or branched alkylene, an alkenylene or a alkynylene chain having at least one and a maximum of five carbon atoms
where the abovementioned alkylene, alkenylene or alkynylene radicals may be partially halogenated and/or may carry one to three of the following groups:
—$OR^4$, —$OCOR^4$, —$OCONHR^4$ or —$OSO_2R^4$ and $X^3$ is a straight-chain or branched alkylene, an alkenylene or an alkynylene chain having a maximum of five carbon atoms
where the abovementioned alkylene, alkenylene or alkynylene radicals may be partially halogenated and/or may carry one to three of the following groups:
—$OR^4$, —$OCOR^4$, —$OCONHR^4$ or —$OSO_2R^4$,
where $X^2OX^3$ builds up the variable $X^1$.

In general, the starting materials are employed in equimolar amounts. However, it may be advantageous to employ an excess of one or another component.

If appropriate, it may be advantageous to carry out the reaction in the presence of a base. The starting materials and the auxiliary base are advantageously employed in equimolar amounts. In certain cases, an excess of the auxiliary base, for example 1.5 to 3 molar equivalents, based on VII, may be advantageous.

Suitable auxiliary bases are tertiary alkylamines such as triethylamine and pyridine, alkali metal carbonates, for example sodium carbonate and potassium carbonate, and alkali metal hydrides, for example sodium hydride. Preference is given to using triethylamine, pyridine and potassium carbonate.

Examples of suitable solvents are chlorinated hydrocarbons such as methylene chloride and 1,2-dichloroethane, aromatic hydrocarbons, for example toluene, xylene, chlorobenzene, ethers such as diethyl ether, methyl tert-butyl ether, tetrahydrofuran, dioxane, polar aprotic solvents such as acetonitrile, dimethylformamide and dimethyl sulfoxide, or esters such as ethyl acetate, or mixtures of these.

The reaction temperature is generally in the range from 0° C. to the boiling point of the reaction mixture.

Work-up can be carried out in a manner known per se.

Emphasis is given to the compounds of the formula I according to the invention where the group $X^1$ is either a $C_1$–$C_2$-alkylene or a $C_2$-alkenylene chain including one further oxygen or sulfur atom and
Het is a three- to six-membered partially or fully saturated heterocyclic group or a three- to six-membered heteroaromatic group having up to three hetero atoms selected from the group consisting of:
nitrogen, oxygen and sulfur,
where the abovementioned heterocyclic or heteroaromatic group may be partially or fully halogenated and/or may be substituted by $R^5$.

Additionally, emphasis is given to the compounds of the formula I according to the invention where the group Het is a five- or six-membered partially or fully saturated heterocyclic or a five- or six-membered heteroaromatic group having up to three hetero atoms selected from the group consisting of nitrogen, oxygen and sulfur, where the abovementioned heterocyclic or heteroaromatic group may be partially or fully halogenated and/or be substituted by $R^5$;

$R^5$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$alkyl-carbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where the alkyl radicals may in each case be substituted by in each case one or more of the following radicals:
cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$alkyl-carbonyloxy, $C_1$–$C_4$-alkyl, $C_1$–$C_4$-haloalkyl, $C_1$–$C_4$alkyl-thio, $C_1$–$C_4$-haloalkylthio, $C_1$–$C_4$-alkoxy, $C_1$–$C_4$-haloalkoxy.

The organic moieties mentioned for the substituents $R^1$–$R^{12}$ or as radicals on phenyl, hetaryl and heterocyclyl rings are collective terms for individual enumerations of the individual group members. All hydrocarbon chains, ie. all alkyl, haloalkyl, cycloalkyl, alkoxyalkyl, alkoxy, haloalkoxy, alkyliminooxy, alkoxyamino, alkylsulfonyl, haloalkylsulfonyl, alkylcarbonyl, haloalkylcarbonyl, alkoxycarbonyl, alkoxyalkoxycarbonyl, alkenyl, cycloalkenyl, alkynyl moieties can be straight-chain or branched. Unless otherwise specified, halogenated substituents preferably carry one to five identical or different halogen atoms, the meaning of halogen being in each case fluorine, chlorine, bromine or iodine.

Examples of other meanings are:

$C_1$–$C_4$-alkyl and the alkyl moieties of $C_1$–$C_4$-alkylcarbonyl: methyl, ethyl, n-propyl, 1-methylethyl, butyl, 1-methylpropyl, 2-methylpropyl and 1,1-dimethylethyl;

$C_1$–$C_6$-alkyl and the alkyl moieties of $C_1$–$C_6$-alkoxy-$C_1$–$C_6$-alkyl and $C_1$–$C_6$-alkylcarbonyl: $C_1$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, eg. chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$$C_6$-haloalkyl and the haloalkyl moieties of $C_1$–$C_6$-haloalkylcarbonyl: $C_1$–$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-alkoxy and the alkoxy moieties of $C_1$–$C_4$-alkoxyamino, $C_1$–$C_4$-alkoxy-$C_2$–$C_6$-alkoxycarbonyl and $C_1$–$C_4$-alkoxycarbonyl: methoxy, ethoxy, propoxy, 1-methylethoxy, butoxy, 1-methylpropoxy, 2-methylpropoxy and 1,1-dimethylethoxy;

$C_1$–$C_6$-alkoxy and the alkoxy moieties of $C_1$–$C_6$-alkoxy-$C_1$–$C_6$-alkyl, $C_1$–$C_6$-alkoxy-$C_2$–$C_6$-alkyl, $C_1$–$C_4$-alkoxy-$C_2$–$C_6$-alkoxycarbonyl and $C_1$–$C_6$-alkoxycarbonyl: $C_1$–$C_4$-alkoxy as mentioned above, and also pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, eg. fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_4$-alkylsulfonyl ($C_1$–$C_4$-alkyl-$S(=O)_2$—): methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl: $C_1$–$C_4$-alkylsulfonyl as mentioned above, and also pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, ie. fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$–$C_4$-alkyliminooxy: methyliminooxy, ethyliminooxy, 1-propyliminooxy, 2-propyliminooxy, 1-butyliminooxy and 2-butyliminooxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl: $C_3$–$C_6$-alkenyl as mentioned above, and also ethenyl;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_2$–$C_6$-alkynyl: $C_3$–$C_6$-alkynyl as mentioned above, and also ethynyl:

$C_3$–$C_6$-cycloalkyl: cyclopropyl, cyclobutyl, cyclopentyl and cyclohexyl;

$C_4$–$C_6$-cycloalkenyl: cyclobuten-1-yl, cyclobuten-3-yl, cyclopenten-1-yl, cyclopenten-3-yl, cyclopenten-4-yl, cyclohexen-1-yl, cyclohexen-3-yl and cyclohexen-4-yl;

heterocyclyl, and also the heterocyclyl radicals in heterocyclyloxy: three- to seven-membered saturated or partially unsaturated mono- or polycyclic heterocycles which contain one to three hetero atoms selected from a group consisting of oxygen, nitrogen and sulfur, such as oxiranyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2—oxazolidinyl, 4-Oxazolidinyl, 5-Oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol- 2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, hetaryl, and also the hetaryl radicals in hetaryloxy:
aromatic mono- or polycyclic radicals which, besides carbon ring members, may additionally contain one to four nitrogen atoms or one to three nitrogen atoms and one oxygen or one sulfur atom or one oxygen and one sulfur atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-Oxazolyl, 4-Oxazolyl, 5-Oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4,5-tetrazin-3-yl, and also the corresponding benzo-fused derivatives.

All phenyl, hetaryl and heterocyclyl rings are preferably unsubstituted or carry one to three halogen atoms and/or one or two radicals selected from the following group: nitro, cyano, methyl, trifluoromethyl, methoxy, trifluoromethoxy or methoxycarbonyl.

With a view to the use of the compounds of the formula I according to the invention as herbicides, the variables preferably have the following meanings, viz. in each case alone or in combination:

$R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^3$ or —$S(O)_nR^3$;
  particularly preferably nitro, halogen such as, for example, fluorine, chlorine or bromine, $C_1$–$C_6$-haloalkyl, —$OR^3$ or —$SO_2R^3$;

$R^2$ is hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^3$ or —$S(O)_nR^3$;
  particularly preferably hydrogen, nitro, halogen such as, for example, fluorine, chlorine or bromine, $C_1$–$C_6$-alkyl, $C_1$–$C_6$-haloalkyl, —$OR^3$ or —$SO_2R^3$;

$R^3$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl;
  particularly preferably hydrogen, $C_1$–$C_4$-alkyl, $C_1$–$C_4$-haloalkyl, $C_2$–$C_3$-alkenyl, $C_2$–$C_3$-alkynyl or phenyl;
  where the abovementioned alkyl radicals may be partially or fully halogenated and/or may carry one to three of the following groups:
  hydroxyl, mercapto, amino, cyano, $R^3$, —$OR^3$, —$SR^3$, —$N(R^3)_2$, =$NOR^3$, —$OCOR^3$, —$SCOR^3$, —$NR^3COR^3$, —$CO_2R^3$, —$COSR^3$, —$CON(R^3)_2$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the eight last mentioned radicals may in turn be substituted;
  also preferred is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl; where the abovementioned alkyl radicals may be partially or fully halogenated and/or may carry one to three of the following groups:
  hydroxyl, mercapto, amino, cyano, $R^{3'}$, —$OR^{3'}$, —$SR^{3'}$, —$N(R^{3'})_2$, =$NOR^{3'}$, —$OCOR^{3'}$, —$SCOR^{3'}$, —$NR^{3'}$—$COR^{3'}$, $CO_2R^{3'}$, —$COSR^{3'}$, —$CON(R^{3'})_2$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the eight last mentioned radicals may in turn be substituted; (wherein $R^{3'}$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl);

n is 0, 1 or 2, particularly preferably 0 or 2;

$X^1$ is a straight-chain or branched $C_1$–$C_4$-alkylene, a $C_2$–$C_4$-alkenylene or a $C_2$–$C_4$-alkynylene chain, particularly preferably an ethylene, propylene, propenylene or propynylene chain which is interrupted by a hetero atom selected from the group consisting of oxygen and sulfur, preferably oxygen,
  where the abovementioned alkylene, alkenylene or alkynylene radicals may be partially halogenated and/or may carry one to three of the following groups:
  —$OR^4$, —$OCOR^4$, —$OCONHR^4$ or —$OSO_2R^4$;

$R^4$ is hydrogen, $C_1$–$C_6$-alkyl or $C_1$–$C_6$-haloalkyl; particularly preferably hydrogen, methyl, ethyl or trifluoromethyl;

$R^5$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where the alkyl radicals may in each case be substituted by in each case one or more of the following radicals:
  cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy.

$R^6$, $R^7$, $R^9$ and $R^{11}$ are each hydrogen or $C_1$–$C_4$-alkyl;
  particularly preferably hydrogen, methyl or ethyl;

$R^8$ is hydrogen, $C_1$–$C_4$-alkyl, $C_3$–$C_4$-cycloalkyl, where the two last mentioned groups may carry one to three of the following substituents: halogen, $C_1$–$C_4$-alkoxy or $C_1$–$C_4$-alkylthio;
  tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,3-oxathiolan-2-yl, 1,3-oxathian-2-yl, 1,3-dithian-2-yl or 1,3-dithiolan-2-yl, where the six last mentioned groups may in each case carry one to three $C_1$–$C_4$-alkyl radicals; particularly preferably hydrogen, methyl, ethyl, cyclopropyl, di(methoxy)methyl, di(ethoxy) methyl, 2-ethylthiopropyl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 5,5-dimethyl-1,3-dioxan-2-yl, 1,3-oxathiolan-2-yl, 1,3-oxathian-2-yl, 1,3-dithiolan-2-yl, 5,5-dimethyl-1,3-dithian-2-yl or 1-methylthiocyclopropyl;

$R^{10}$ is hydrogen, $C_1$–$C_4$-alkyl or $C_1$–$C_4$-alkoxycarbonyl;
  particularly preferably hydrogen, methyl or methoxycarbonyl.

Likewise, it may be advantageous for $R^8$ and $R^{11}$ to form a π bond, thus giving rise to a double bond system.

Alternatively, the $CR^8R^9$ unit may advantageously be replaced by C=O.

Particular preference is given to the compounds of the formula Ia, where $R^1$ is attached in position 2 and $R^2$ is attached in position 4 of the phenyl ring.

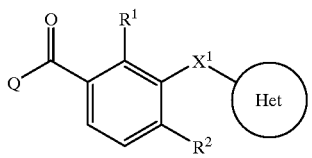

Most particular preference is given to the compounds of the formula Ia in which the substituents $R^1$, $R^2$ and Q are each as defined above, $X^1$ is a $C_1$–$C_2$-alkylene or a $C_2$-alkynylene chain containing one further oxygen and Het is a three- to six-membered, preferably a five- or six-membered, partially or fully saturated heterocyclic group or a three- to six-membered, preferably a five- or six-membered, heteroaromatic group having up to three hetero atoms, particularly preferably having one or two hetero atoms selected from the following three groups:
nitrogen,
oxygen in combination with at least one nitrogen or
sulfur in combination with at least one nitrogen,
particularly preferably from the following two groups:
nitrogen or
oxygen in combination with at least one nitrogen,
where the abovementioned heterocyclic or heteroaromatic group may be partially or fully halogenated and/or may be substituted by $R^5$.

Furthermore, most particular preference is given to compounds of the formula Ia according to the invention in which the substituents $R^1$, $R^2$ and $X^1$ are each as defined above and Het is a five- or six-membered partially or fully saturated heterocyclic group or a five- or six-membered heteroaromatic group having up to three hetero atoms, particularly preferably having one or two hetero atoms selected from the following three groups:
nitrogen,
oxygen in combination with at least one nitrogen or
sulfur in combination with at least one nitrogen,
particularly preferably from the following two groups:
nitrogen or
oxygen in combination with at least one nitrogen,
where the abovementioned heterocyclic or heteroaromatic group may be partially or fully halogenated and/or may be substituted by $R^5$.

Particular preference is given to the compounds Ib of Tables 1 to 36.

TABLE A

| No. | $X^{1*}$ | Het |
|---|---|---|
| 1 | $OCH_2$ | oxiranyl |
| 2 | $OCH_2$ | 3-methyl-2-oxiranyl |
| 3 | $OCH_2$ | 2-oxetanyl |
| 4 | $OCH_2$ | 3-hydroxy-3-methyl-2-oxetanyl |
| 5 | $OCH_2$ | 3-hydroxy-3-ethyl-2-oxetanyl |
| 6 | $OCH_2$ | 3-hydroxy-3-propyl-2-oxetanyl |
| 7 | $OCH_2$ | 3-hydroxy-3-butyl-2-oxetanyl |
| 8 | $OCH_2$ | 3-methoxy-3-methyl-2-oxetanyl |
| 9 | $OCH_2$ | 3-methoxy-3-ethyl-2-oxetanyl |
| 10 | $OCH_2$ | 3-methoxy-3-propyl-2-oxetanyl |
| 11 | $OCH_2$ | 3-methoxy-3-butyl-2-oxetanyl |
| 12 | $OCH_2$ | 3-trimethylsilyl-oxy-3-methyl-2-oxetanyl |
| 13 | $OCH_2$ | 3-trimethylsilyl-oxy-3-ethyl-2-oxetanyl |
| 14 | $OCH_2$ | 3-trimethylsilyl-oxy-3-propyl-2-oxetanyl |
| 15 | $OCH_2$ | 3-trimethylsilyl-oxy-3-butyl-2-oxetanyl |
| 16 | $OCH_2$ | 3-oxetanyl |
| 17 | $OCH_2$ | 2-furyl |
| 18 | $OCH_2$ | 4,5-dihydro-2-furyl |
| 19 | $OCH_2$ | 2,3-dihydro-2-furyl |
| 20 | $OCH_2$ | 3-furyl |
| 21 | $OCH_2$ | 4,5-dihydro-3-furyl |
| 22 | $OCH_2$ | 2,3-dihydro-3-furyl |
| 23 | $OCH_2$ | 2-thienyl |
| 24 | $OCH_2$ | 4,5-dihydro-2-thienyl |
| 25 | $OCH_2$ | 2,3-dihydro-2-thienyl |
| 26 | $OCH_2$ | 5-chloro-2-thienyl |
| 27 | $OCH_2$ | 5-methyl-2-thienyl |
| 28 | $OCH_2$ | 3-thienyl |
| 29 | $OCH_2$ | 4,5-dihydro-3-thienyl |
| 30 | $OCH_2$ | 2,3-dihydro-3-thienyl |
| 31 | $OCH_2$ | 2-pyrrolyl |
| 32 | $OCH_2$ | 2,5-dihydro-2-pyrrolyl |
| 33 | $OCH_2$ | 3-pyrrolyl |
| 34 | $OCH_2$ | 2,5-dihydro-3-pyrrolyl |
| 35 | $OCH_2$ | 3-isoxazolyl |
| 36 | $OCH_2$ | 4-methyl-3-isoxazolyl |
| 37 | $OCH_2$ | 5-methyl-3-isoxazolyl |
| 38 | $OCH_2$ | 4,5-dimethyl-3-isoxazolyl |
| 39 | $OCH_2$ | 4,5-dihydro-3-isoxazolyl |
| 40 | $OCH_2$ | 4-methyl-4,5-dihydro-3-isoxazolyl |
| 41 | $OCH_2$ | 5-methyl-4,5-dihydro-3-isoxazolyl |
| 42 | $OCH_2$ | 4,5-dimethyl-4,5-dihydro-3-isoxazolyl |
| 43 | $OCH_2$ | 4-isoxazolyl |
| 44 | $OCH_2$ | 3-methyl-4-isoxazolyl |
| 45 | $OCH_2$ | 5-methyl-4-isoxazolyl |
| 46 | $OCH_2$ | 5-cyclopropyl-4-isoxazolyl |
| 47 | $OCH_2$ | 5-phenyl-4-isoxazolyl |
| 48 | $OCH_2$ | 3,5-dimethyl-4-isoxazolyl |
| 49 | $OCH_2$ | 4,5-dihydro-4-isoxazolyl |
| 50 | $OCH_2$ | 3-methyl-4,5-dihydro-4-isoxazolyl |
| 51 | $OCH_2$ | 5-methyl-4,5-dihydro-4-isoxazolyl |
| 52 | $OCH_2$ | 3,5-dimethyl-4,5-dihydro-4-isoxazolyl |
| 53 | $OCH_2$ | 5-isoxazolyl |
| 54 | $OCH_2$ | 3-methyl-5-isoxazolyl |
| 55 | $OCH_2$ | 4-methyl-5-isoxazolyl |
| 56 | $OCH_2$ | 3,4-dimethyl-5-isoxazolyl |
| 57 | $OCH_2$ | 4,5-dihydro-5-isoxazolyl |
| 58 | $OCH_2$ | 3-methyl-4,5-dihydro-5-isoxazolyl |
| 59 | $OCH_2$ | 4-methyl-4,5-dihydro-5-isoxazolyl |
| 60 | $OCH_2$ | 3,4-dimethyl-4,5-dihydro-5-isoxazolyl |
| 61 | $OCH_2$ | 3-isothiazolyl |
| 62 | $OCH_2$ | 4-methyl-3-isothiazolyl |
| 63 | $OCH_2$ | 5-methyl-3-isothiazolyl |
| 64 | $OCH_2$ | 4-isothiazolyl |
| 65 | $OCH_2$ | 3-methyl-4-isothiazolyl |
| 66 | $OCH_2$ | 5-methyl-4-isothiazolyl |
| 67 | $OCH_2$ | 5-isothiazolyl |
| 68 | $OCH_2$ | 3-methyl-5-isothiazolyl |
| 69 | $OCH_2$ | 4-methyl-5-isothiazolyl |
| 70 | $OCH_2$ | 2-oxazolyl |
| 71 | $OCH_2$ | 4-oxazolyl |
| 72 | $OCH_2$ | 5-oxazolyl |
| 73 | $OCH_2$ | 2-thiazolyl |
| 74 | $OCH_2$ | 4-thiazolyl |
| 75 | $OCH_2$ | 5-thiazolyl |
| 76 | $OCH_2$ | 3-pyrazolyl |
| 77 | $OCH_2$ | 4-pyrazolyl |
| 78 | $OCH_2$ | 1-methyl-3-pyrazolyl |
| 79 | $OCH_2$ | 1-methyl-4-pyrazolyl |
| 80 | $OCH_2$ | 1-methyl-5-pyrazolyl |
| 81 | $OCH_2$ | 2-imidazolyl |
| 82 | $OCH_2$ | 1-methyl-2-imidazolyl |
| 83 | $OCH_2$ | 5-methyl-[1,3,4]-2-oxadiazolyl |
| 84 | $OCH_2$ | 5-methyl-[1,2,4]-3-oxadiazolyl |
| 85 | $OCH_2$ | 5-methyl-[1,3,4]-2-thiadiazolyl |

TABLE A-continued

| No. | $X^{1*}$ | Het |
|---|---|---|
| 86 | OCH$_2$ | 5-methyl-[1,2,4]-3-thiadiazolyl |
| 87 | OCH$_2$ | [1,2,4]-3-triazolyl |
| 88 | OCH$_2$ | [1,2,3]-4-triazolyl |
| 89 | OCH$_2$ | 2-pyridyl |
| 90 | OCH$_2$ | 6-chloro-2-pyridyl |
| 91 | OCH$_2$ | 6-methoxy-2-pyridyl |
| 92 | OCH$_2$ | 6-trifluoromethyl-2-pyridyl |
| 93 | OCH$_2$ | 3-pyridyl |
| 94 | OCH$_2$ | 2-chloro-3-pyridyl |
| 95 | OCH$_2$ | 2-methoxy-3-pyridyl |
| 96 | OCH$_2$ | 4-pyridyl |
| 97 | OCH$_2$ | 2-chloro-4-pyridyl |
| 98 | OCH$_2$ | 2-methoxy-4-pyridyl |
| 99 | OCH$_2$ | 2-ethoxy-4-pyridyl |
| 100 | OCH$_2$ | 2-methylthio-4-pyridyl |
| 101 | OCH$_2$ | 2-trifluoromethyl-5-pyridyl |
| 102 | OCH$_2$ | 2-pyrimidinyl |
| 103 | OCH$_2$ | 3-pyrimidinyl |
| 104 | OCH$_2$ | 4-pyrimidinyl |
| 105 | OCH$_2$ | 2-pyrazinyl |
| 106 | OCH$_2$ | 3-pyridazinyl |
| 107 | OCH$_2$ | 4-pyridazinyl |
| 108 | OCH$_2$ | 2-(2H-1,3-oxazinyl) |
| 109 | OCH$_2$ | 2-(6H-1,3-oxazinyl) |
| 110 | OCH$_2$ | 4-(6H-1,3-oxazinyl) |
| 111 | OCH$_2$ | 6-(6H-1,3-oxazinyl) |
| 112 | OCH$_2$ | [1,3,5]-2-triazinyl |
| 113 | OCH$_2$ | [1,2,4]-3-triazinyl |
| 114 | OCH$_2$ | [1,2,4]-5-triazinyl |
| 115 | OCH$_2$ | [1,2,4]-6-triazinyl |
| 116 | CH$_2$O | oxiranyl |
| 117 | CH$_2$O | 3-methyl-2-oxiranyl |
| 118 | CH$_2$O | 2-oxetanyl |
| 119 | CH$_2$O | 3-hydroxy-3-methyl-2-oxetanyl |
| 120 | CH$_2$O | 3-hydroxy-3-ethyl-2-oxetanyl |
| 121 | CH$_2$O | 3-hydroxy-3-propyl-2-oxetanyl |
| 122 | CH$_2$O | 3-hydroxy-3-butyl-2-oxetanyl |
| 123 | CH$_2$O | 3-methoxy-3-methyl-2-oxetanyl |
| 124 | CH$_2$O | 3-methoxy-3-ethyl-2-oxetanyl |
| 125 | CH$_2$O | 3-methoxy-3-propyl-2-oxetanyl |
| 126 | CH$_2$O | 3-methoxy-3-butyl-2-oxetanyl |
| 127 | CH$_2$O | 3-trimethylsilyl-oxy-3-methyl-2-oxetanyl |
| 128 | CH$_2$O | 3-trimethylsilyl-oxy-3-ethyl-2-oxetanyl |
| 129 | CH$_2$O | 3-trimethylsilyl-oxy-3-propyl-2-oxetanyl |
| 130 | CH$_2$O | 3-trimethylsilyl-oxy-3-butyl-2-oxetanyl |
| 131 | CH$_2$O | 3-oxetanyl |
| 132 | CH$_2$O | 2-furyl |
| 133 | CH$_2$O | 4,5-dihydro-2-furyl |
| 134 | CH$_2$O | 2,3-dihydro-2-furyl |
| 135 | CH$_2$O | 3-furyl |
| 136 | CH$_2$O | 4,5-dihydro-3-furyl |
| 137 | CH$_2$O | 2,3-dihydro-3-furyl |
| 138 | CH$_2$O | 2-thienyl |
| 139 | CH$_2$O | 4,5-dihydro-2-thienyl |
| 140 | CH$_2$O | 2,3-dihydro-2-thienyl |
| 141 | CH$_2$O | 5-chloro-2-thienyl |
| 142 | CH$_2$O | 5-methyl-2-thienyl |
| 143 | CH$_2$O | 3-thienyl |
| 144 | CH$_2$O | 4,5-dihydro-3-thienyl |
| 145 | CH$_2$O | 2,3-dihydro-3-thienyl |
| 146 | CH$_2$O | 2-pyrrolyl |
| 147 | CH$_2$O | 2,5-dihydro-2-pyrrolyl |
| 148 | CH$_2$O | 3-pyrrolyl |
| 149 | CH$_2$O | 2,5-dihydro-3-pyrrolyl |
| 150 | CH$_2$O | 3-isoxazolyl |
| 151 | CH$_2$O | 4-methyl-3-isoxazolyl |
| 152 | CH$_2$O | 5-methyl-3-isoxazolyl |
| 153 | CH$_2$O | 4,5-dimethyl-3-isoxazolyl |
| 154 | CH$_2$O | 4,5-dihydro-3-isoxazolyl |
| 155 | CH$_2$O | 4-methyl-4,5-dihydro-3-isoxazolyl |
| 156 | CH$_2$O | 5-methyl-4,5-dihydro-3-isoxazolyl |
| 157 | CH$_2$O | 4,5-dimethyl-4,5-dihydro-3-isoxazolyl |
| 158 | CH$_2$O | 4-isoxazolyl |
| 159 | CH$_2$O | 3-methyl-4-isoxazolyl |
| 160 | CH$_2$O | 5-methyl-4-isoxazolyl |
| 161 | CH$_2$O | 5-cyclopropyl-4-isoxazolyl |
| 162 | CH$_2$O | 5-phenyl-4-isoxazolyl |
| 163 | CH$_2$O | 3,5-dimethyl-4-isoxazolyl |
| 164 | CH$_2$O | 4,5-dihydro-4-isoxazolyl |
| 165 | CH$_2$O | 3-methyl-4,5-dihydro-4-isoxazolyl |
| 166 | CH$_2$O | 5-methyl-4,5-dihydro-4-isoxazolyl |
| 167 | CH$_2$O | 3,5-dimethyl-4,5-dihydro-4-isoxazolyl |
| 168 | CH$_2$O | 5-isoxazolyl |
| 169 | CH$_2$O | 3-methyl-5-isoxazolyl |
| 170 | CH$_2$O | 4-methyl-5-isoxazolyl |
| 171 | CH$_2$O | 3,4-dimethyl-5-isoxazolyl |
| 172 | CH$_2$O | 4,5-dihydro-5-isoxazolyl |
| 173 | CH$_2$O | 3-methyl-4,5-dihydro-5-isoxazolyl |
| 174 | CH$_2$O | 4-methyl-4,5-dihydro-5-isoxazolyl |
| 175 | CH$_2$O | 3,4-dimethyl-4,5-dihydro-5-isoxazolyl |
| 176 | CH$_2$O | 3-isothiazolyl |
| 177 | CH$_2$O | 4-methyl-3-isothiazolyl |
| 178 | CH$_2$O | 5-methyl-3-isothiazolyl |
| 179 | CH$_2$O | 4-isothiazolyl |
| 180 | CH$_2$O | 3-methyl-4-isothiazolyl |
| 181 | CH$_2$O | 5-methyl-4-isothiazolyl |
| 182 | CH$_2$O | 5-isothiazolyl |
| 183 | CH$_2$O | 3-methyl-5-isothiazolyl |
| 184 | CH$_2$O | 4-methyl-5-isothiazolyl |
| 185 | CH$_2$O | 2-oxazolyl |
| 186 | CH$_2$O | 4-oxazolyl |
| 187 | CH$_2$O | 5-oxazolyl |
| 188 | CH$_2$O | 2-thiazolyl |
| 189 | CH$_2$O | 4-thiazolyl |
| 190 | CH$_2$O | 5-thiazolyl |
| 191 | CH$_2$O | 3-pyrazolyl |
| 192 | CH$_2$O | 4-pyrazolyl |
| 193 | CH$_2$O | 1-methyl-3-pyrazolyl |
| 194 | CH$_2$O | 1-methyl-4-pyrazolyl |
| 195 | CH$_2$O | 1-methyl-5-pyrazolyl |
| 196 | CH$_2$O | 2-imidazolyl |
| 197 | CH$_2$O | 1-methyl-2-imidazolyl |
| 198 | CH$_2$O | 5-methyl-[1,3,4]-2-oxadiazolyl |
| 199 | CH$_2$O | 5-methyl-[1,2,4]-3-oxadiazolyl |
| 200 | CH$_2$O | 5-methyl-[1,3,4]-2-thiadiazolyl |
| 201 | CH$_2$O | 5-methyl-[1,2,4]-3-thiadiazolyl |
| 202 | CH$_2$O | [1,2,4]-3-triazolyl |
| 203 | CH$_2$O | [1,2,3]-4-triazolyl |
| 204 | CH$_2$O | 2-pyridyl |
| 205 | CH$_2$O | 6-chloro-2-pyridyl |
| 206 | CH$_2$O | 6-methoxy-2-pyridyl |
| 207 | CH$_2$O | 6-trifluoromethyl-2-pyridyl |
| 208 | CH$_2$O | 3-pyridyl |
| 209 | CH$_2$O | 2-chloro-3-pyridyl |
| 210 | CH$_2$O | 2-methoxy-3-pyridyl |
| 211 | CH$_2$O | 4-pyridyl |
| 212 | CH$_2$O | 2-chloro-4-pyridyl |
| 213 | CH$_2$O | 2-methoxy-4-pyridyl |
| 214 | CH$_2$O | 2-ethoxy-4-pyridyl |
| 215 | CH$_2$O | 2-methylthio-4-pyridyl |
| 216 | CH$_2$O | 2-trifluoromethyl-5-pyridyl |
| 217 | CH$_2$O | 2-pyrimidinyl |
| 218 | CH$_2$O | 3-pyrimidinyl |
| 219 | CH$_2$O | 4-pyrimidinyl |
| 220 | CH$_2$O | 2-pyrazinyl |
| 221 | CH$_2$O | 3-pyridazinyl |
| 222 | CH$_2$O | 4-pyridazinyl |
| 223 | CH$_2$O | 2-(2H-1,3-oxazinyl) |
| 224 | CH$_2$O | 2-(6H-1,3-oxazinyl) |
| 225 | CH$_2$O | 4-(6H-1,3-oxazinyl) |
| 226 | CH$_2$O | 6-(6H-1,3-oxazinyl) |
| 227 | CH$_2$O | [1,3,5]-2-triazinyl |
| 228 | CH$_2$O | [1,2,4]-3-triazinyl |
| 229 | CH$_2$O | [1,2,4]-5-triazinyl |
| 230 | CH$_2$O | [1,2,4]-6-triazinyl |
| 231 | OCH$_2$CH$_2$ | oxiranyl |
| 232 | OCH$_2$CH$_2$ | 3-methyl-2-oxiranyl |

TABLE A-continued

| No. | X¹* | Het |
|---|---|---|
| 233 | OCH$_2$CH$_2$ | 2-oxetanyl |
| 234 | OCH$_2$CH$_2$ | 3-hydroxy-3-methyl-2-oxetanyl |
| 235 | OCH$_2$CH$_2$ | 3-hydroxy-3-ethyl-2-oxetanyl |
| 236 | OCH$_2$CH$_2$ | 3-hydroxy-3-propyl-2-oxetanyl |
| 237 | OCH$_2$CH$_2$ | 3-hydroxy-3-butyl-2-oxetanyl |
| 238 | OCH$_2$CH$_2$ | 3-methoxy-3-methyl-2-oxetanyl |
| 239 | OCH$_2$CH$_2$ | 3-methoxy-3-ethyl-2-oxetanyl |
| 240 | OCH$_2$CH$_2$ | 3-methoxy-3-propyl-2-oxetanyl |
| 241 | OCH$_2$CH$_2$ | 3-methoxy-3-butyl-2-oxetanyl |
| 242 | OCH$_2$CH$_2$ | 3-trimethylsilyl-oxy-3-methyl-2-oxetanyl |
| 243 | OCH$_2$CH$_2$ | 3-trimethylsilyl-oxy-3-ethyl-2-oxetanyl |
| 244 | OCH$_2$CH$_2$ | 3-trimethylsilyl-oxy-3-propyl-2-oxetanyl |
| 245 | OCH$_2$CH$_2$ | 3-trimethylsilyl-oxy-3-butyl-2-oxetanyl |
| 246 | OCH$_2$CH$_2$ | 3-oxetanyl |
| 247 | OCH$_2$CH$_2$ | 2-furyl |
| 248 | OCH$_2$CH$_2$ | 4,5-dihydro-2-furyl |
| 249 | OCH$_2$CH$_2$ | 2,3-dihydro-2-furyl |
| 250 | OCH$_2$CH$_2$ | 3-furyl |
| 251 | OCH$_2$CH$_2$ | 4,5-dihydro-3-furyl |
| 252 | OCH$_2$CH$_2$ | 2,3-dihydro-3-furyl |
| 253 | OCH$_2$CH$_2$ | 2-thienyl |
| 254 | OCH$_2$CH$_2$ | 4,5-dihydro-2-thienyl |
| 255 | OCH$_2$CH$_2$ | 2,3-dihydro-2-thienyl |
| 256 | OCH$_2$CH$_2$ | 5-chloro-2-thienyl |
| 257 | OCH$_2$CH$_2$ | 5-methyl-2-thienyl |
| 258 | OCH$_2$CH$_2$ | 3-thienyl |
| 259 | OCH$_2$CH$_2$ | 4,5-dihydro-3-thienyl |
| 260 | OCH$_2$CH$_2$ | 2,3-dihydro-3-thienyl |
| 261 | OCH$_2$CH$_2$ | 2-pyrrolyl |
| 262 | OCH$_2$CH$_2$ | 2,5-dihydro-2-pyrrolyl |
| 263 | OCH$_2$CH$_2$ | 3-pyrrolyl |
| 264 | OCH$_2$CH$_2$ | 2,5-dihydro-3-pyrrolyl |
| 265 | OCH$_2$CH$_2$ | 3-isoxazolyl |
| 266 | OCH$_2$CH$_2$ | 4-methyl-3-isoxazolyl |
| 267 | OCH$_2$CH$_2$ | 5-methyl-3-isoxazolyl |
| 268 | OCH$_2$CH$_2$ | 4,5-dimethyl-3-isoxazolyl |
| 269 | OCH$_2$CH$_2$ | 4,5-dihydro-3-isoxazolyl |
| 270 | OCH$_2$CH$_2$ | 4-methyl-4,5-dihydro-3-isoxazolyl |
| 271 | OCH$_2$CH$_2$ | 5-methyl-4,5-dihydro-3-isoxazolyl |
| 272 | OCH$_2$CH$_2$ | 4,5-dimethyl-4,5-di-hydro-3-isoxazolyl |
| 273 | OCH$_2$CH$_2$ | 4-isoxazolyl |
| 274 | OCH$_2$CH$_2$ | 3-methyl-4-isoxazolyl |
| 275 | OCH$_2$CH$_2$ | 5-methyl-4-isoxazolyl |
| 276 | OCH$_2$CH$_2$ | 5-cyclopropyl-4-isoxazolyl |
| 277 | OCH$_2$CH$_2$ | 5-phenyl-4-isoxazolyl |
| 278 | OCH$_2$CH$_2$ | 3,5-dimethyl-4-isoxazolyl |
| 279 | OCH$_2$CH$_2$ | 4,5-dihydro-4-isoxazolyl |
| 280 | OCH$_2$CH$_2$ | 3-methyl-4,5-dihydro-4-isoxazolyl |
| 281 | OCH$_2$CH$_2$ | 5-methyl-4,5-dihydro-4-isoxazolyl |
| 282 | OCH$_2$CH$_2$ | 3,5-dimethyl-4,5-di-hydro-4-isoxazolyl |
| 283 | OCH$_2$CH$_2$ | 5-isoxazolyl |
| 284 | OCH$_2$CH$_2$ | 3-methyl-5-isoxazolyl |
| 285 | OCH$_2$CH$_2$ | 4-methyl-5-isoxazolyl |
| 286 | OCH$_2$CH$_2$ | 3,4-dimethyl-5-isoxazolyl |
| 287 | OCH$_2$CH$_2$ | 4,5-dihydro-5-isoxazolyl |
| 288 | OCH$_2$CH$_2$ | 3-methyl-4,5-dihydro-5-isoxazolyl |
| 289 | OCH$_2$CH$_2$ | 4-methyl-4,5-dihydro-5-isoxazolyl |
| 290 | OCH$_2$CH$_2$ | 3,4-dimethyl-4,5-di-hydro-5-isoxazolyl |
| 291 | OCH$_2$CH$_2$ | 3-isothiazolyl |
| 292 | OCH$_2$CH$_2$ | 4-methyl-3-isothiazolyl |
| 293 | OCH$_2$CH$_2$ | 5-methyl-3-isothiazolyl |
| 294 | OCH$_2$CH$_2$ | 4-isothiazolyl |
| 295 | OCH$_2$CH$_2$ | 3-methyl-4-isothiazolyl |
| 296 | OCH$_2$CH$_2$ | 5-methyl-4-isothiazolyl |
| 297 | OCH$_2$CH$_2$ | 5-isothiazolyl |
| 298 | OCH$_2$CH$_2$ | 3-methyl-5-isothiazolyl |
| 299 | OCH$_2$CH$_2$ | 4-methyl-5-isothiazolyl |
| 300 | OCH$_2$CH$_2$ | 2-oxazolyl |
| 301 | OCH$_2$CH$_2$ | 4-oxazolyl |
| 302 | OCH$_2$CH$_2$ | 5-oxazolyl |
| 303 | OCH$_2$CH$_2$ | 2-thiazolyl |
| 304 | OCH$_2$CH$_2$ | 4-thiazolyl |
| 305 | OCH$_2$CH$_2$ | 5-thiazolyl |
| 306 | OCH$_2$CH$_2$ | 3-pyrazolyl |
| 307 | OCH$_2$CH$_2$ | 4-pyrazolyl |
| 308 | OCH$_2$CH$_2$ | 1-methyl-3-pyrazolyl |
| 309 | OCH$_2$CH$_2$ | 1-methyl-4-pyrazolyl |
| 310 | OCH$_2$CH$_2$ | 1-methyl-5-pyrazolyl |
| 311 | OCH$_2$CH$_2$ | 2-imidazolyl |
| 312 | OCH$_2$CH$_2$ | 1-methyl-2-imidazolyl |
| 313 | OCH$_2$CH$_2$ | 5-methyl-[1,3,4]-2-oxadiazolyl |
| 314 | OCH$_2$CH$_2$ | 5-methyl-[1,2,4]-3-oxadiazolyl |
| 315 | OCH$_2$CH$_2$ | 5-methyl-[1,3,4]-2-thiadiazolyl |
| 316 | OCH$_2$CH$_2$ | 5-methyl-[1,2,4]-3-thiadiazolyl |
| 317 | OCH$_2$CH$_2$ | [1,2,4]-3-triazolyl |
| 318 | OCH$_2$CH$_2$ | [1,2,3]-4-triazolyl |
| 319 | OCH$_2$CH$_2$ | 2-pyridyl |
| 320 | OCH$_2$CH$_2$ | 6-chloro-2-pyridyl |
| 321 | OCH$_2$CH$_2$ | 6-methoxy-2-pyridyl |
| 322 | OCH$_2$CH$_2$ | 6-trifluoromethyl-2-pyridyl |
| 323 | OCH$_2$CH$_2$ | 3-pyridyl |
| 324 | OCH$_2$CH$_2$ | 2-chloro-3-pyridyl |
| 325 | OCH$_2$CH$_2$ | 2-methoxy-3-pyridyl |
| 326 | OCH$_2$CH$_2$ | 4-pyridyl |
| 327 | OCH$_2$CH$_2$ | 2-chloro-4-pyridyl |
| 328 | OCH$_2$CH$_2$ | 2-methoxy-4-pyridyl |
| 329 | OCH$_2$CH$_2$ | 2-ethoxy-4-pyridyl |
| 330 | OCH$_2$CH$_2$ | 2-methylthio-4-pyridyl |
| 331 | OCH$_2$CH$_2$ | 2-trifluoromethyl-5-pyridyl |
| 332 | OCH$_2$CH$_2$ | 2-pyrimidinyl |
| 333 | OCH$_2$CH$_2$ | 3-pyrimidinyl |
| 334 | OCH$_2$CH$_2$ | 4-pyrimidinyl |
| 335 | OCH$_2$CH$_2$ | 2-pyrazinyl |
| 336 | OCH$_2$CH$_2$ | 3-pyridazinyl |
| 337 | OCH$_2$CH$_2$ | 4-pyridazinyl |
| 338 | OCH$_2$CH$_2$ | 2-(2H-1,3-oxazinyl) |
| 339 | OCH$_2$CH$_2$ | 2-(6H-1,3-oxazinyl) |
| 340 | OCH$_2$CH$_2$ | 4-(6H-1,3-oxazinyl) |
| 341 | OCH$_2$CH$_2$ | 6-(6H-1,3-oxazinyl) |
| 342 | OCH$_2$CH$_2$ | [1,3,5]-2-triazinyl |
| 343 | OCH$_2$CH$_2$ | [1,2,4]-3-triazinyl |
| 344 | OCH$_2$CH$_2$ | [1,2,4]-5-triazinyl |
| 345 | OCH$_2$CH$_2$ | [1,2,4]-6-triazinyl |
| 346 | CH$_2$CH$_2$O | oxiranyl |
| 347 | CH$_2$CH$_2$O | 3-methyl-2-oxiranyl |
| 348 | CH$_2$CH$_2$O | 2-oxetanyl |
| 349 | CH$_2$CH$_2$O | 3-hydroxy-3-methyl-2-oxetanyl |
| 350 | CH$_2$CH$_2$O | 3-hydroxy-3-ethyl-2-oxetanyl |
| 351 | CH$_2$CH$_2$O | 3-hydroxy-3-propyl-2-oxetanyl |
| 352 | CH$_2$CH$_2$O | 3-hydroxy-3-butyl-2-oxetanyl |
| 353 | CH$_2$CH$_2$O | 3-methoxy-3-methyl-2-oxetanyl |
| 354 | CH$_2$CH$_2$O | 3-methoxy-3-ethyl-2-oxetanyl |
| 355 | CH$_2$CH$_2$O | 3-methoxy-3-propyl-2-oxetanyl |
| 356 | CH$_2$CH$_2$O | 3-methoxy-3-butyl-2-oxetanyl |
| 357 | CH$_2$CH$_2$O | 3-trimethylsilyl-oxy-3-methyl-2-oxetanyl |
| 358 | CH$_2$CH$_2$O | 3-trimethylsilyl-oxy-3-ethyl-2-oxetanyl |
| 359 | CH$_2$CH$_2$O | 3-trimethylsilyl-oxy-3-propyl-2-oxetanyl |
| 360 | CH$_2$CH$_2$O | 3-trimethylsilyl-oxy-3-butyl-2-oxetanyl |
| 361 | CH$_2$CH$_2$O | 3-oxetanyl |
| 362 | CH$_2$CH$_2$O | 2-furyl |
| 363 | CH$_2$CH$_2$O | 4,5-dihydro-2-furyl |
| 364 | CH$_2$CH$_2$O | 2,3-dihydro-2-furyl |
| 365 | CH$_2$CH$_2$O | 3-furyl |
| 366 | CH$_2$CH$_2$O | 4,5-dihydro-3-furyl |
| 367 | CH$_2$CH$_2$O | 2,3-dihydro-3-furyl |
| 368 | CH$_2$CH$_2$O | 2-thienyl |
| 369 | CH$_2$CH$_2$O | 4,5-dihydro-2-thienyl |
| 370 | CH$_2$CH$_2$O | 2,3-dihydro-2-thienyl |
| 371 | CH$_2$CH$_2$O | 5-chloro-2-thienyl |
| 372 | CH$_2$CH$_2$O | 5-methyl-2-thienyl |
| 373 | CH$_2$CH$_2$O | 3-thienyl |
| 374 | CH$_2$CH$_2$O | 4,5-dihydro-3-thienyl |
| 375 | CH$_2$CH$_2$O | 2,3-dihydro-3-thienyl |

TABLE A-continued

| No. | X[1]* | Het |
|---|---|---|
| 376 | CH$_2$CH$_2$O | 2-pyrrolyl |
| 377 | CH$_2$CH$_2$O | 2,5-dihydro-2-pyrrolyl |
| 378 | CH$_2$CH$_2$O | 3-pyrrolyl |
| 379 | CH$_2$CH$_2$O | 2,5-dihydro-3-pyrrolyl |
| 380 | CH$_2$CH$_2$O | 3-isoxazolyl |
| 381 | CH$_2$CH$_2$O | 4-methyl-3-isoxazolyl |
| 382 | CH$_2$CH$_2$O | 5-methyl-3-isoxazolyl |
| 383 | CH$_2$CH$_2$O | 4,5-dimethyl-3-isoxazolyl |
| 384 | CH$_2$CH$_2$O | 4,5-dihydro-3-isoxazolyl |
| 385 | CH$_2$CH$_2$O | 4-methyl-4,5-dihydro-3-isoxazolyl |
| 386 | CH$_2$CH$_2$O | 5-methyl-4,5-dihydro-3-isoxazolyl |
| 387 | CH$_2$CH$_2$O | 4,5-dimethyl-4,5-di-hydro-3-isoxazolyl |
| 388 | CH$_2$CH$_2$O | 4-isoxazolyl |
| 389 | CH$_2$CH$_2$O | 3-methyl-4-isoxazolyl |
| 390 | CH$_2$CH$_2$O | 5-methyl-4-isoxazolyl |
| 391 | CH$_2$CH$_2$O | 5-cyclopropyl-4-isoxazolyl |
| 392 | CH$_2$CH$_2$O | 5-phenyl-4-isoxazolyl |
| 393 | CH$_2$CH$_2$O | 3,5-dimethyl-4-isoxazolyl |
| 394 | CH$_2$CH$_2$O | 4,5-dihydro-4-isoxazolyl |
| 395 | CH$_2$CH$_2$O | 3-methyl-4,5-dihydro-4-isoxazolyl |
| 396 | CH$_2$CH$_2$O | 5-methyl-4,5-dihydro-4-isoxazolyl |
| 397 | CH$_2$CH$_2$O | 3,5-dimethyl-4,5-di-hydro-4-isoxazolyl |
| 398 | CH$_2$CH$_2$O | 5-isoxazolyl |
| 399 | CH$_2$CH$_2$O | 3-methyl-5-isoxazolyl |
| 400 | CH$_2$CH$_2$O | 4-methyl-5-isoxazolyl |
| 401 | CH$_2$CH$_2$O | 3,4-dimethyl-5-isoxazolyl |
| 402 | CH$_2$CH$_2$O | 4,5-dihydro-5-isoxazolyl |
| 403 | CH$_2$CH$_2$O | 3-methyl-4,5-dihydro-5-isoxazolyl |
| 404 | CH$_2$CH$_2$O | 4-methyl-4,5-dihydro-5-isoxazolyl |
| 405 | CH$_2$CH$_2$O | 3,4-dimethyl-4,5-di-hydro-5-isoxazolyl |
| 406 | CH$_2$CH$_2$O | 3-isothiazolyl |
| 407 | CH$_2$CH$_2$O | 4-methyl-3-isothiazolyl |
| 408 | CH$_2$CH$_2$O | 5-methyl-3-isothiazolyl |
| 409 | CH$_2$CH$_2$O | 4-isothiazolyl |
| 410 | CH$_2$CH$_2$O | 3-methyl-4-isothiazolyl |
| 411 | CH$_2$CH$_2$O | 5-methyl-4-isothiazolyl |
| 412 | CH$_2$CH$_2$O | 5-isothiazolyl |
| 413 | CH$_2$CH$_2$O | 3-methyl-5-isothiazolyl |
| 414 | CH$_2$CH$_2$O | 4-methyl-5-isothiazolyl |
| 415 | CH$_2$CH$_2$O | 2-oxazolyl |
| 416 | CH$_2$CH$_2$O | 4-oxazolyl |
| 417 | CH$_2$CH$_2$O | 5-oxazolyl |
| 418 | CH$_2$CH$_2$O | 2-thiazolyl |
| 419 | CH$_2$CH$_2$O | 4-thiazolyl |
| 420 | CH$_2$CH$_2$O | 5-thiazolyl |
| 421 | CH$_2$CH$_2$O | 3-pyrazolyl |
| 422 | CH$_2$CH$_2$O | 4-pyrazolyl |
| 423 | CH$_2$CH$_2$O | 1-methyl-3-pyrazolyl |
| 424 | CH$_2$CH$_2$O | 1-methyl-4-pyrazolyl |
| 425 | CH$_2$CH$_2$O | 1-methyl-5-pyrazolyl |
| 426 | CH$_2$CH$_2$O | 2-imidazolyl |
| 427 | CH$_2$CH$_2$O | 1-methyl-2-imidazolyl |
| 428 | CH$_2$CH$_2$O | 5-methyl-[1,3,4]-2-oxadiazolyl |
| 429 | CH$_2$CH$_2$O | 5-methyl-[1,2,4]-3-oxadiazolyl |
| 430 | CH$_2$CH$_2$O | 5-methyl-[1,3,4]-2-thiadiazolyl |
| 431 | CH$_2$CH$_2$O | 5-methyl-[1,2,4]-3-thiadiazolyl |
| 432 | CH$_2$CH$_2$O | [1,2,4]-3-triazolyl |
| 433 | CH$_2$CH$_2$O | [1,2,3]-4-triazolyl |
| 434 | CH$_2$CH$_2$O | 2-pyridyl |
| 435 | CH$_2$CH$_2$O | 6-chloro-2-pyridyl |
| 436 | CH$_2$CH$_2$O | 6-methoxy-2-pyridyl |
| 437 | CH$_2$CH$_2$O | 6-trifluoromethyl-2-pyridyl |
| 438 | CH$_2$CH$_2$O | 3-pyridyl |
| 439 | CH$_2$CH$_2$O | 2-chloro-3-pyridyl |
| 440 | CH$_2$CH$_2$O | 2-methoxy-3-pyridyl |
| 441 | CH$_2$CH$_2$O | 4-pyridyl |
| 442 | CH$_2$CH$_2$O | 2-chloro-4-pyridyl |
| 443 | CH$_2$CH$_2$O | 2-methoxy-4-pyridyl |
| 444 | CH$_2$CH$_2$O | 2-ethoxy-4-pyridyl |
| 445 | CH$_2$CH$_2$O | 2-methylthio-4-pyridyl |
| 446 | CH$_2$CH$_2$O | 2-trifluoromethyl-5-pyridyl |
| 447 | CH$_2$CH$_2$O | 2-pyrimidinyl |
| 448 | CH$_2$CH$_2$O | 3-pyrimidinyl |
| 449 | CH$_2$CH$_2$O | 4-pyrimidinyl |
| 450 | CH$_2$CH$_2$O | 2-pyrazinyl |
| 451 | CH$_2$CH$_2$O | 3-pyridazinyl |
| 452 | CH$_2$CH$_2$O | 4-pyridazinyl |
| 453 | CH$_2$CH$_2$O | 2-(2H-1,3-oxazinyl) |
| 454 | CH$_2$CH$_2$O | 2-(6H-1,3-oxazinyl) |
| 455 | CH$_2$CH$_2$O | 4-(6H-1,3-oxazinyl) |
| 456 | CH$_2$CH$_2$O | 6-(6H-1,3-oxazinyl) |
| 457 | CH$_2$CH$_2$O | [1,3,5]-2-triazinyl |
| 458 | CH$_2$CH$_2$O | [1,2,4]-3-triazinyl |
| 459 | CH$_2$CH$_2$O | [1,2,4]-5-triazinyl |
| 460 | CH$_2$CH$_2$O | [1,2,4]-6-triazinyl |
| 461 | CH$_2$OCH$_2$ | oxiranyl |
| 462 | CH$_2$OCH$_2$ | 3-methyl-2-oxiranyl |
| 463 | CH$_2$OCH$_2$ | 2-oxetanyl |
| 464 | CH$_2$OCH$_2$ | 3-hydroxy-3-methyl-2-oxetanyl |
| 465 | CH$_2$OCH$_2$ | 3-hydroxy-3-ethyl-2-oxetanyl |
| 466 | CH$_2$OCH$_2$ | 3-hydroxy-3-propyl-2-oxetanyl |
| 467 | CH$_2$OCH$_2$ | 3-hydroxy-3-butyl-2-oxetanyl |
| 468 | CH$_2$OCH$_2$ | 3-methoxy-3-methyl-2-oxetanyl |
| 469 | CH$_2$OCH$_2$ | 3-methoxy-3-ethyl-2-oxetanyl |
| 470 | CH$_2$OCH$_2$ | 3-methoxy-3-propyl-2-oxetanyl |
| 471 | CH$_2$OCH$_2$ | 3-methoxy-3-butyl-2-oxetanyl |
| 472 | CH$_2$OCH$_2$ | 3-trimethylsilyl-oxy-3-methyl-2-oxetanyl |
| 473 | CH$_2$OCH$_2$ | 3-trimethylsilyl-oxy-3-ethyl-2-oxetanyl |
| 474 | CH$_2$OCH$_2$ | 3-trimethylsilyl-oxy-3-propyl-2-oxetanyl |
| 475 | CH$_2$OCH$_2$ | 3-trimethylsilyl-oxy-3-butyl-2-oxetanyl |
| 476 | CH$_2$OCH$_2$ | 3-oxetanyl |
| 477 | CH$_2$OCH$_2$ | 2-furyl |
| 478 | CH$_2$OCH$_2$ | 4,5-dihydro-2-furyl |
| 479 | CH$_2$OCH$_2$ | 2,3-dihydro-2-furyl |
| 480 | CH$_2$OCH$_2$ | 3-furyl |
| 481 | CH$_2$OCH$_2$ | 4,5-dihydro-3-furyl |
| 482 | CH$_2$OCH$_2$ | 2,3-dihydro-3-furyl |
| 483 | CH$_2$OCH$_2$ | 2-thienyl |
| 484 | CH$_2$OCH$_2$ | 4,5-dihydro-2-thienyl |
| 485 | CH$_2$OCH$_2$ | 2,3-dihydro-2-thienyl |
| 486 | CH$_2$OCH$_2$ | 5-chloro-2-thienyl |
| 487 | CH$_2$OCH$_2$ | 5-methyl-2-thienyl |
| 489 | CH$_2$OCH$_2$ | 4,5-dihydro-3-thienyl |
| 490 | CH$_2$OCH$_2$ | 2,3-dihydro-3-thienyl |
| 491 | CH$_2$OCH$_2$ | 2-pyrrolyl |
| 492 | CH$_2$OCH$_2$ | 2,5-dihydro-3-pyrrolyl |
| 493 | CH$_2$OCH$_2$ | 3-pyrrolyl |
| 494 | CH$_2$OCH$_2$ | 2,5-dihydro-3-pyrrolyl |
| 495 | CH$_2$OCH$_2$ | 3-isoxazolyl |
| 496 | CH$_2$OCH$_2$ | 4-methyl-3-isoxazolyl |
| 497 | CH$_2$OCH$_2$ | 5-methyl-3-isoxazolyl |
| 498 | CH$_2$OCH$_2$ | 4,5-dimethyl-3-isoxazolyl |
| 499 | CH$_2$OCH$_2$ | 4,5-dihydro-3-isoxazolyl |
| 500 | CH$_2$OCH$_2$ | 4-methyl-4,5-dihydro-3-isoxazolyl |
| 501 | CH$_2$OCH$_2$ | 5-methyl-4,5-dihydro-3-isoxazolyl |
| 502 | CH$_2$OCH$_2$ | 4,5-dimethyl-4,5-di-hydro-3-isoxazolyl |
| 503 | CH$_2$OCH$_2$ | 4-isoxazolyl |
| 504 | CH$_2$OCH$_2$ | 3-methyl-4-isoxazolyl |
| 505 | CH$_2$OCH$_2$ | 5-methyl-4-isoxazolyl |
| 506 | CH$_2$OCH$_2$ | 5-cyclopropyl-4-isoxazolyl |
| 507 | CH$_2$OCH$_2$ | 5-phenyl-4-isoxazolyl |
| 508 | CH$_2$OCH$_2$ | 3,5-dimethyl-4-isoxazolyl |
| 509 | CH$_2$OCH$_2$ | 4,5-dihydro-4-isoxazolyl |
| 510 | CH$_2$OCH$_2$ | 3-methyl-4,5-dihydro-4-isoxazolyl |
| 511 | CH$_2$OCH$_2$ | 5-methyl-4,5-dihydro-4-isoxazolyl |
| 512 | CH$_2$OCH$_2$ | 3,5-dimethyl-4,5-di-hydro-4-isoxazolyl |
| 513 | CH$_2$OCH$_2$ | 5-isoxazolyl |
| 514 | CH$_2$OCH$_2$ | 3-methyl-5-isoxazolyl |
| 515 | CH$_2$OCH$_2$ | 4-methyl-5-isoxazolyl |
| 516 | CH$_2$OCH$_2$ | 3,4-dimethyl-5-isoxazolyl |
| 517 | CH$_2$OCH$_2$ | 4,5-dihydro-5-isoxazolyl |
| 518 | CH$_2$OCH$_2$ | 3-methyl-4,5-dihydro-5-isoxazolyl |
| 519 | CH$_2$OCH$_2$ | 4-methyl-4,5-dihydro-5-isoxazolyl |
| 520 | CH$_2$OCH$_2$ | 3,4-dimethyl-4,5-di-hydro-5-isoxazolyl |

TABLE A-continued

| No. | X¹* | Het |
|---|---|---|
| 521 | $CH_2OCH_2$ | 3-isothiazolyl |
| 522 | $CH_2OCH_2$ | 4-methyl-3-isothiazolyl |
| 523 | $CH_2OCH_2$ | 5-methyl-3-isothiazolyl |
| 524 | $CH_2OCH_2$ | 4-isothiazolyl |
| 525 | $CH_2OCH_2$ | 3-methyl-4-isothiazolyl |
| 526 | $CH_2OCH_2$ | 5-methyl-4-isothiazolyl |
| 527 | $CH_2OCH_2$ | 5-isothiazolyl |
| 528 | $CH_2OCH_2$ | 3-methyl-5-isothiazolyl |
| 529 | $CH_2OCH_2$ | 4-methyl-5-isothiazolyl |
| 530 | $CH_2OCH_2$ | 2-oxazolyl |
| 531 | $CH_2OCH_2$ | 4-oxazolyl |
| 532 | $CH_2OCH_2$ | 5-oxazolyl |
| 533 | $CH_2OCH_2$ | 2-thiazolyl |
| 534 | $CH_2OCH_2$ | 4-thiazolyl |
| 535 | $CH_2OCH_2$ | 5-thiazolyl |
| 536 | $CH_2OCH_2$ | 3-pyrazolyl |
| 537 | $CH_2OCH_2$ | 4-pyrazolyl |
| 538 | $CH_2OCH_2$ | 1-methyl-3-pyrazolyl |
| 539 | $CH_2OCH_2$ | 1-methyl-4-pyrazolyl |
| 540 | $CH_2OCH_2$ | 1-methyl-5-pyrazolyl |
| 541 | $CH_2OCH_2$ | 2-imidazolyl |
| 542 | $CH_2OCH_2$ | 1-methyl-2-imidazolyl |
| 543 | $CH_2OCH_2$ | 5-methyl-[1,3,4]-2-oxadiazolyl |
| 544 | $CH_2OCH_2$ | 5-methyl-[1,2,4]-3-oxadiazolyl |
| 545 | $CH_2OCH_2$ | 5-methyl-[1,3,4]-2-thiadiazolyl |
| 546 | $CH_2OCH_2$ | 5-methyl-[1,2,4]-3-thiadiazolyl |
| 547 | $CH_2OCH_2$ | [1,2,4]-3-triazolyl |
| 548 | $CH_2OCH_2$ | [1,2,3]-4-triazolyl |
| 549 | $CH_2OCH_2$ | 2-pyridyl |
| 550 | $CH_2OCH_2$ | 6-chloro-2-pyridyl |
| 551 | $CH_2OCH_2$ | 6-methoxy-2-pyridyl |
| 552 | $CH_2OCH_2$ | 6-trifluoromethyl-2-pyridyl |
| 553 | $CH_2OCH_2$ | 3-pyridyl |
| 554 | $CH_2OCH_2$ | 2-chloro-3-pyridyl |
| 555 | $CH_2OCH_2$ | 2-methoxy-3-pyridyl |
| 556 | $CH_2OCH_2$ | 4-pyridyl |
| 557 | $CH_2OCH_2$ | 2-chloro-4-pyridyl |
| 558 | $CH_2OCH_2$ | 2-methoxy-4-pyridyl |
| 559 | $CH_2OCH_2$ | 2-ethoxy-4-pyridyl |
| 560 | $CH_2OCH_2$ | 2-methylthio-4-pyridyl |
| 561 | $CH_2OCH_2$ | 2-trifluoromethyl-5-pyridyl |
| 562 | $CH_2OCH_2$ | 2-pyrimidinyl |
| 563 | $CH_2OCH_2$ | 3-pyrimidinyl |
| 564 | $CH_2OCH_2$ | 4-pyrimidinyl |
| 565 | $CH_2OCH_2$ | 2-pyrazinyl |
| 566 | $CH_2OCH_2$ | 3-pyridazinyl |
| 567 | $CH_2OCH_2$ | 4-pyridazinyl |
| 568 | $CH_2OCH_2$ | 2-(2H-1,3-oxazinyl) |
| 569 | $CH_2OCH_2$ | 2-(6H-1,3-oxazinyl) |
| 570 | $CH_2OCH_2$ | 4-(6H-1,3-oxazinyl) |
| 571 | $CH_2OCH_2$ | 6-(6H-1,3-oxazinyl) |
| 572 | $CH_2OCH_2$ | [1,3,5]-2-triazinyl |
| 573 | $CH_2OCH_2$ | [1,2,4]-3-triazinyl |
| 574 | $CH_2OCH_2$ | [1,2,4]-5-triazinyl |
| 575 | $CH_2OCH_2$ | [1,2,4]-6-triazinyl |
| 576 | $CH_2OCH_2CH=CH$ | oxiranyl |
| 577 | $CH_2OCH_2CH=CH$ | 3-methyl-2-oxiranyl |
| 578 | $CH_2OCH_2CH=CH$ | 2-oxetanyl |
| 579 | $CH_2OCH_2CH=CH$ | 3-hydroxy-3-methyl-2-oxetanyl |
| 580 | $CH_2OCH_2CH=CH$ | 3-hydroxy-3-ethyl-2-oxetanyl |
| 581 | $CH_2OCH_2CH=CH$ | 3-hydroxy-3-propyl-2-oxetanyl |
| 582 | $CH_2OCH_2CH=CH$ | 3-hydroxy-3-butyl-2-oxetanyl |
| 583 | $CH_2OCH_2CH=CH$ | 3-methoxy-3-methyl-2-oxetanyl |
| 584 | $CH_2OCH_2CH=CH$ | 3-methoxy-3-ethyl-2-oxetanyl |
| 585 | $CH_2OCH_2CH=CH$ | 3-methoxy-3-propyl-2-oxetanyl |
| 586 | $CH_2OCH_2CH=CH$ | 3-methoxy-3-butyl-2-oxetanyl |
| 587 | $CH_2OCH_2CH=CH$ | 3-trimethylsilyloxy-3-methyl-2-oxetanyl |
| 588 | $CH_2OCH_2CH=CH$ | 3-trimethylsilyloxy-3-ethyl-2-oxetanyl |
| 589 | $CH_2OCH_2CH=CH$ | 3-trimethylsilyloxy-3-propyl-2-oxetanyl |
| 590 | $CH_2OCH_2CH=CH$ | 3-trimethylsilyloxy-3-butyl-2-oxetanyl |
| 591 | $CH_2OCH_2CH=CH$ | 3-oxetanyl |
| 592 | $CH_2OCH_2CH=CH$ | 2-furyl |
| 593 | $CH_2OCH_2CH=CH$ | 4,5-dihydro-2-furyl |
| 594 | $CH_2OCH_2CH=CH$ | 2,3-dihydro-2-furyl |
| 595 | $CH_2OCH_2CH=CH$ | 3-furyl |
| 596 | $CH_2OCH_2CH=CH$ | 4,5-dihydro-3-furyl |
| 597 | $CH_2OCH_2CH=CH$ | 2,3-dihydro-3-furyl |
| 598 | $CH_2OCH_2CH=CH$ | 2-thienyl |
| 599 | $CH_2OCH_2CH=CH$ | 4,5-dihydro-2-thienyl |
| 600 | $CH_2OCH_2CH=CH$ | 2,3-dihydro-2-thienyl |
| 601 | $CH_2OCH_2CH=CH$ | 5-chloro-2-thienyl |
| 602 | $CH_2OCH_2CH=CH$ | 5-methyl-2-thienyl |
| 603 | $CH_2OCH_2CH=CH$ | 3-thienyl |
| 604 | $CH_2OCH_2CH=CH$ | 4,5-dihydro-3-thienyl |
| 605 | $CH_2OCH_2CH=CH$ | 2,3-dihydro-3-thienyl |
| 606 | $CH_2OCH_2CH=CH$ | 2-pyrrolyl |
| 607 | $CH_2OCH_2CH=CH$ | 2,5-dihydro-2-pyrrolyl |
| 608 | $CH_2OCH_2CH=CH$ | 3-pyrrolyl |
| 609 | $CH_2OCH_2CH=CH$ | 2,5-dihydro-3-pyrrolyl |
| 610 | $CH_2OCH_2CH=CH$ | 3-isoxazolyl |
| 611 | $CH_2OCH_2CH=CH$ | 4-methyl-3-isoxazolyl |
| 612 | $CH_2OCH_2CH=CH$ | 5-methyl-3-isoxazolyl |
| 613 | $CH_2OCH_2CH=CH$ | 4,5-dimethyl-3-isoxazolyl |
| 614 | $CH_2OCH_2CH=CH$ | 4,5-dihydro-3-isoxazolyl |
| 615 | $CH_2OCH_2CH=CH$ | 4-methyl-4,5-dihydro-3-isoxazolyl |
| 616 | $CH_2OCH_2CH=CH$ | 5-methyl-4,5-dihydro-3-isoxazolyl |
| 617 | $CH_2OCH_2CH=CH$ | 4,5-dimethyl-4,5-dihydro-3-isoxazolyl |
| 618 | $CH_2OCH_2CH=CH$ | 4-isoxazolyl |
| 619 | $CH_2OCH_2CH=CH$ | 3-methyl-4-isoxazolyl |
| 620 | $CH_2OCH_2CH=CH$ | 5-methyl-4-isoxazolyl |
| 621 | $CH_2OCH_2CH=CH$ | 5-cyclopropyl-4-isoxazolyl |
| 622 | $CH_2OCH_2CH=CH$ | 5-phenyl-4-isoxazolyl |
| 623 | $CH_2OCH_2CH=CH$ | 3,5-dimethyl-4-isoxazolyl |
| 624 | $CH_2OCH_2CH=CH$ | 4,5-dihydro-4-isoxazolyl |
| 625 | $CH_2OCH_2CH=CH$ | 3-methyl-4,5-dihydro-4-isoxazolyl |
| 626 | $CH_2OCH_2CH=CH$ | 5-methyl-4,5-dihydro-4-isoxazolyl |
| 627 | $CH_2OCH_2CH=CH$ | 3,5-dimethyl-4,5-dihydro-4-isoxazolyl |
| 628 | $CH_2OCH_2CH=CH$ | 5-isoxazolyl |
| 629 | $CH_2OCH_2CH=CH$ | 3-methyl-5-isoxazolyl |
| 630 | $CH_2OCH_2CH=CH$ | 4-methyl-5-isoxazolyl |
| 631 | $CH_2OCH_2CH=CH$ | 3,4-dimethyl-5-isoxazolyl |
| 632 | $CH_2OCH_2CH=CH$ | 4,5-dihydro-5-isoxazolyl |
| 633 | $CH_2OCH_2CH=CH$ | 3-methyl-4,5-dihydro-5-isoxazolyl |
| 634 | $CH_2OCH_2CH=CH$ | 4-methyl-4,5-dihydro-5-isoxazolyl |
| 635 | $CH_2OCH_2CH=CH$ | 3,4-dimethyl-4,5-dihydro-5-isoxazolyl |
| 636 | $CH_2OCH_2CH=CH$ | 3-isothiazolyl |
| 637 | $CH_2OCH_2CH=CH$ | 4-methyl-3-isothiazolyl |
| 638 | $CH_2OCH_2CH=CH$ | 5-methyl-3-isothiazolyl |
| 639 | $CH_2OCH_2CH=CH$ | 4-isothiazolyl |
| 640 | $CH_2OCH_2CH=CH$ | 3-methyl-4-isothiazolyl |
| 641 | $CH_2OCH_2CH=CH$ | 5-methyl-4-isothiazolyl |
| 642 | $CH_2OCH_2CH=CH$ | 5-isothiazolyl |
| 643 | $CH_2OCH_2CH=CH$ | 3-methyl-5-isothiazolyl |
| 644 | $CH_2OCH_2CH=CH$ | 4-methyl-5-isothiazolyl |
| 645 | $CH_2OCH_2CH=CH$ | 2-oxazolyl |
| 646 | $CH_2OCH_2CH=CH$ | 4-oxazolyl |
| 647 | $CH_2OCH_2CH=CH$ | 5-oxazolyl |
| 648 | $CH_2OCH_2CH=CH$ | 2-thiazolyl |
| 649 | $CH_2OCH_2CH=CH$ | 4-thiazolyl |
| 650 | $CH_2OCH_2CH=CH$ | 5-thiazolyl |
| 651 | $CH_2OCH_2CH=CH$ | 3-pyrazolyl |
| 652 | $CH_2OCH_2CH=CH$ | 4-pyrazolyl |
| 653 | $CH_2OCH_2CH=CH$ | 1-methyl-3-pyrazolyl |
| 654 | $CH_2OCH_2CH=CH$ | 1-methyl-4-pyrazolyl |
| 655 | $CH_2OCH_2CH=CH$ | 1-methyl-5-pyrazolyl |
| 656 | $CH_2OCH_2CH=CH$ | 2-imidazolyl |
| 657 | $CH_2OCH_2CH=CH$ | 1-methyl-2-imidazolyl |
| 658 | $CH_2OCH_2CH=CH$ | 5-methyl-[1,3,4]-2-oxadiazolyl |
| 659 | $CH_2OCH_2CH=CH$ | 5-methyl-[1,2,4]-3-oxadiazolyl |
| 660 | $CH_2OCH_2CH=CH$ | 5-methyl-[1,3,4]-2-thiadiazolyl |
| 661 | $CH_2OCH_2CH=CH$ | 5-methyl-[1,2,4]-3-thiadiazolyl |
| 662 | $CH_2OCH_2CH=CH$ | [1,2,4]-3-triazolyl |
| 663 | $CH_2OCH_2CH=CH$ | [1,2,3]-4-triazolyl |
| 664 | $CH_2OCH_2CH=CH$ | 2-pyridyl |
| 665 | $CH_2OCH_2CH=CH$ | 6-chloro-2-pyridyl |
| 666 | $CH_2OCH_2CH=CH$ | 6-methoxy-2-pyridyl |
| 667 | $CH_2OCH_2CH=CH$ | 6-trifluoromethyl-2-pyridyl |

TABLE A-continued

| No. | X¹* | Het |
|---|---|---|
| 668 | CH₂OCH₂CH=CH | 3-pyridyl |
| 669 | CH₂OCH₂CH=CH | 2-chloro-3-pyridyl |
| 670 | CH₂OCH₂CH=CH | 2-methoxy-3-pyridyl |
| 671 | CH₂OCH₂CH=CH | 4-pyridyl |
| 672 | CH₂OCH₂CH=CH | 2-chloro-4-pyridyl |
| 673 | CH₂OCH₂CH=CH | 2-methoxy-4-pyridyl |
| 674 | CH₂OCH₂CH=CH | 2-ethoxy-4-pyridyl |
| 675 | CH₂OCH₂CH=CH | 2-methylthio-4-pyridyl |
| 676 | CH₂OCH₂CH=CH | 2-trifluoromethyl-5-pyridyl |
| 677 | CH₂OCH₂CH=CH | 2-pyrimidinyl |
| 678 | CH₂OCH₂CH=CH | 3-pyrimidinyl |
| 679 | CH₂OCH₂CH=CH | 4-pyrimidinyl |
| 680 | CH₂OCH₂CH=CH | 2-pyrazinyl |
| 681 | CH₂OCH₂CH=CH | 3-pyridazinyl |
| 682 | CH₂OCH₂CH=CH | 4-pyridazinyl |
| 683 | CH₂OCH₂CH=CH | 2-(2H-1,3-oxazinyl) |
| 684 | CH₂OCH₂CH=CH | 2-(6H-1,3-oxazinyl) |
| 685 | CH₂OCH₂CH=CH | 4-(6H-1,3-oxazinyl) |
| 686 | CH₂OCH₂CH=CH | 6-(6H-1,3-oxazinyl) |
| 687 | CH₂OCH₂CH=CH | [1,3,5]-2-triazinyl |
| 688 | CH₂OCH₂CH=CH | [1,2,4]-3-triazinyl |
| 689 | CH₂OCH₂CH=CH | [1,2,4]-5-triazinyl |
| 690 | CH₂OCH₂CH=CH | [1,2,4]-6-triazinyl |
| 691 | CH=CHCH₂O | oxiranyl |
| 692 | CH=CHCH₂O | 3-methyl-2-oxiranyl |
| 693 | CH=CHCH₂O | 2-oxetanyl |
| 694 | CH=CHCH₂O | 3-hydroxy-3-methyl-2-oxetanyl |
| 695 | CH=CHCH₂O | 3-hydroxy-3-ethyl-2-oxetanyl |
| 696 | CH=CHCH₂O | 3-hydroxy-3-propyl-2-oxetanyl |
| 697 | CH=CHCH₂O | 3-hydroxy-3-butyl-2-oxetanyl |
| 698 | CH=CHCH₂O | 3-methoxy-3-methyl-2-oxetanyl |
| 699 | CH=CHCH₂O | 3-methoxy-3-ethyl-2-oxetanyl |
| 700 | CH=CHCH₂O | 3-methoxy-3-propyl-2-oxetanyl |
| 701 | CH=CHCH₂O | 3-methoxy-3-butyl-2-oxetanyl |
| 702 | CH=CHCH₂O | 3-trimethylsilyloxy-3-methyl-2-oxetanyl |
| 703 | CH=CHCH₂O | 3-trimethylsilyloxy-3-ethyl-2-oxetanyl |
| 704 | CH=CHCH₂O | 3-trimethylsilyloxy-3-propyl-2-oxetanyl |
| 705 | CH=CHCH₂O | 3-trimethylsilyloxy-3-butyl-2-oxetanyl |
| 706 | CH=CHCH₂O | 3-oxetanyl |
| 707 | CH=CHCH₂O | 2-furyl |
| 708 | CH=CHCH₂O | 4,5-dihydro-2-furyl |
| 709 | CH=CHCH₂O | 2,3-dihydro-2-furyl |
| 710 | CH=CHCH₂O | 3-furyl |
| 711 | CH=CHCH₂O | 4,5-dihydro-3-furyl |
| 712 | CH=CHCH₂O | 2,3-dihydro-3-furyl |
| 713 | CH=CHCH₂O | 2-thienyl |
| 714 | CH=CHCH₂O | 4,5-dihydro-2-thienyl |
| 715 | CH=CHCH₂O | 2,3-dihydro-2-thienyl |
| 716 | CH=CHCH₂O | 5-chloro-2-thienyl |
| 717 | CH=CHCH₂O | 5-methyl-2-thienyl |
| 718 | CH=CHCH₂O | 3-thienyl |
| 719 | CH=CHCH₂O | 4,5-dihydro-3-thienyl |
| 720 | CH=CHCH₂O | 2,3-dihydro-3-thienyl |
| 721 | CH=CHCH₂O | 2-pyrrolyl |
| 722 | CH=CHCH₂O | 2,5-dihydro-2-pyrrolyl |
| 723 | CH=CHCH₂O | 3-pyrrolyl |
| 724 | CH=CHCH₂O | 2,5-dihydro-3-pyrrolyl |
| 725 | CH=CHCH₂O | 3-isoxazolyl |
| 726 | CH=CHCH₂O | 4-methyl-3-isoxazolyl |
| 727 | CH=CHCH₂O | 5-methyl-3-isoxazolyl |
| 728 | CH=CHCH₂O | 4,5-dimethyl-3-isoxazolyl |
| 729 | CH=CHCH₂O | 4,5-dihydro-3-isoxazolyl |
| 730 | CH=CHCH₂O | 4-methyl-4,5-dihydro-3-isoxazolyl |
| 731 | CH=CHCH₂O | 5-methyl-4,5-dihydro-3-isoxazolyl |
| 732 | CH=CHCH₂O | 4,5-dimethyl-4,5-dihydro-3-isoxazolyl |
| 733 | CH=CHCH₂O | 4-isoxazolyl |
| 734 | CH=CHCH₂O | 3-methyl-4-isoxazolyl |
| 735 | CH=CHCH₂O | 5-methyl-4-isoxazolyl |
| 736 | CH=CHCH₂O | 5-cyclopropyl-4-isoxazolyl |
| 737 | CH=CHCH₂O | 5-phenyl-4-isoxazolyl |
| 738 | CH=CHCH₂O | 3,5-dimethyl-4-isoxazolyl |
| 739 | CH=CHCH₂O | 4,5-dihydro-4-isoxazolyl |
| 740 | CH=CHCH₂O | 3-methyl-4,5-dihydro-4-isoxazolyl |
| 741 | CH=CHCH₂O | 5-methyl-4,5-dihydro-4-isoxazolyl |
| 742 | CH=CHCH₂O | 3,5-dimethyl-4,5-dihydro-4-isoxazolyl |
| 743 | CH=CHCH₂O | 5-isoxazolyl |
| 744 | CH=CHCH₂O | 3-methyl-5-isoxazolyl |
| 745 | CH=CHCH₂O | 4-methyl-5-isoxazolyl |
| 746 | CH=CHCH₂O | 3,4-dimethyl-5-isoxazolyl |
| 747 | CH=CHCH₂O | 4,5-dihydro-5-isoxazolyl |
| 748 | CH=CHCH₂O | 3-methyl-4,5-dihydro-5-isoxazolyl |
| 749 | CH=CHCH₂O | 4-methyl-4,5-dihydro-5-isoxazolyl |
| 750 | CH=CHCH₂O | 3,4-dimethyl-4,5-dihydro-5-isoxazolyl |
| 751 | CH=CHCH₂O | 3-isothiazolyl |
| 752 | CH=CHCH₂O | 4-methyl-3-isothiazolyl |
| 753 | CH=CHCH₂O | 5-methyl-3-isothiazolyl |
| 754 | CH=CHCH₂O | 4-isothiazolyl |
| 755 | CH=CHCH₂O | 3-methyl-4-isothiazolyl |
| 756 | CH=CHCH₂O | 5-methyl-4-isothiazolyl |
| 757 | CH=CHCH₂O | 5-isothiazolyl |
| 758 | CH=CHCH₂O | 3-methyl-5-isothiazolyl |
| 759 | CH=CHCH₂O | 4-methyl-5-isothiazolyl |
| 760 | CH=CHCH₂O | 2-oxazolyl |
| 761 | CH=CHCH₂O | 4-oxazolyl |
| 762 | CH=CHCH₂O | 5-oxazolyl |
| 763 | CH=CHCH₂O | 2-thiazolyl |
| 764 | CH=CHCH₂O | 4-thiazolyl |
| 765 | CH=CHCH₂O | 5-thiazolyl |
| 766 | CH=CHCH₂O | 3-pyrazolyl |
| 767 | CH=CHCH₂O | 4-pyrazolyl |
| 768 | CH=CHCH₂O | 1-methyl-3-pyrazolyl |
| 769 | CH=CHCH₂O | 1-methyl-4-pyrazolyl |
| 770 | CH=CHCH₂O | 1-methyl-5-pyrazolyl |
| 771 | CH=CHCH₂O | 2-imidazolyl |
| 772 | CH=CHCH₂O | 1-methyl-2-imidazolyl |
| 773 | CH=CHCH₂O | 5-methyl-[1,3,4]-2-oxadiazolyl |
| 774 | CH=CHCH₂O | 5-methyl-[1,2,4]-3-oxadiazolyl |
| 775 | CH=CHCH₂O | 5-methyl-[1,3,4]-2-thiadiazolyl |
| 776 | CH=CHCH₂O | 5-methyl-[1,2,4]-3-thiadiazolyl |
| 777 | CH=CHCH₂O | [1,2,4]-3-triazolyl |
| 778 | CH=CHCH₂O | [1,2,3]-4-triazolyl |
| 779 | CH=CHCH₂O | 2-pyridyl |
| 780 | CH=CHCH₂O | 6-chloro-2-pyridyl |
| 781 | CH=CHCH₂O | 6-methoxy-2-pyridyl |
| 782 | CH=CHCH₂O | 6-trifluoromethyl-2-pyridyl |
| 783 | CH=CHCH₂O | 3-pyridyl |
| 784 | CH=CHCH₂O | 2-chloro-3-pyridyl |
| 785 | CH=CHCH₂O | 2-methoxy-3-pyridyl |
| 786 | CH=CHCH₂O | 4-pyridyl |
| 787 | CH=CHCH₂O | 2-chloro-4-pyridyl |
| 788 | CH=CHCH₂O | 2-methoxy-4-pyridyl |
| 789 | CH=CHCH₂O | 2-ethoxy-4-pyridyl |
| 790 | CH=CHCH₂O | 2-methylthio-4-pyridyl |
| 791 | CH=CHCH₂O | 2-trifluoromethyl-5-pyridyl |
| 792 | CH=CHCH₂O | 2-pyrimidinyl |
| 793 | CH=CHCH₂O | 3-pyrimidinyl |
| 794 | CH=CHCH₂O | 4-pyrimidinyl |
| 795 | CH=CHCH₂O | 2-pyrazinyl |
| 796 | CH=CHCH₂O | 3-pyridazinyl |
| 797 | CH=CHCH₂O | 4-pyridazinyl |
| 798 | CH=CHCH₂O | 2-(2H-1,3-oxazinyl) |
| 799 | CH=CHCH₂O | 2-(6H-1,3-oxazinyl) |
| 800 | CH=CHCH₂O | 4-(6H-1,3-oxazinyl) |
| 801 | CH=CHCH₂O | 6-(6H-1,3-oxazinyl) |
| 802 | CH=CHCH₂O | [1,3,5]-2-triazinyl |
| 803 | CH=CHCH₂O | [1,2,4]-3-triazinyl |
| 804 | CH=CHCH₂O | [1,2,4]-5-triazinyl |
| 805 | CH=CHCH₂O | [1,2,4]-6-triazinyl |
| 806 | C≡C—CH₂O | oxiranyl |
| 807 | C≡C—CH₂O | 3-methyl-2-oxiranyl |
| 808 | C≡C—CH₂O | 2-oxetanyl |
| 809 | C≡C—CH₂O | 3-hydroxy-3-methyl-2-oxetanyl |
| 810 | C≡C—CH₂O | 3-hydroxy-3-ethyl-2-oxetanyl |
| 811 | C≡C—CH₂O | 3-hydroxy-3-propyl-2-oxetanyl |
| 812 | C≡C—CH₂O | 3-hydroxy-3-butyl-2-oxetanyl |
| 813 | C≡C—CH₂O | 3-methoxy-3-methyl-2-oxetanyl |
| 814 | C≡C—CH₂O | 3-methoxy-3-ethyl-2-oxetanyl |

TABLE A-continued

| No. | X¹* | Het |
|---|---|---|
| 815 | C≡C—CH₂O | 3-methoxy-3-propyl-2-oxetanyl |
| 816 | C≡C—CH₂O | 3-methoxy-3-butyl-2-oxetanyl |
| 817 | C≡C—CH₂O | 3-trimethylsilyl-oxy-3-methyl-2-oxetanyl |
| 818 | C≡C—CH₂O | 3-trimethylsilyl-oxy-3-ethyl-2-oxetanyl |
| 819 | C≡C—CH₂O | 3-trimethylsilyl-oxy-3-propyl-2-oxetanyl |
| 820 | C≡C—CH₂O | 3-trimethylsilyl-oxy-3-butyl-2-oxetanyl |
| 821 | C≡C—CH₂O | 3-oxetanyl |
| 822 | C≡C—CH₂O | 2-furyl |
| 823 | C≡C—CH₂O | 4,5-dihydro-2-furyl |
| 824 | C≡C—CH₂O | 2,3-dihydro-2-furyl |
| 825 | C≡C—CH₂O | 3-furyl |
| 826 | C≡C—CH₂O | 4,5-dihydro-3-furyl |
| 827 | C≡C—CH₂O | 2,3-dihydro-3-furyl |
| 828 | C≡C—CH₂O | 2-thienyl |
| 829 | C≡C—CH₂O | 4,5-dihydro-2-thienyl |
| 830 | C≡C—CH₂O | 2,3-dihydro-2-thienyl |
| 831 | C≡C—CH₂O | 5-chloro-2-thienyl |
| 832 | C≡C—CH₂O | 5-methyl-2-thienyl |
| 833 | C≡C—CH₂O | 3-thienyl |
| 834 | C≡C—CH₂O | 4,5-dihydro-3-thienyl |
| 835 | C≡C—CH₂O | 2,3-dihydro-3-thienyl |
| 836 | C≡C—CH₂O | 2-pyrrolyl |
| 837 | C≡C—CH₂O | 2,5-dihydro-2-pyrrolyl |
| 838 | C≡C—CH₂O | 3-pyrrolyl |
| 839 | C≡C—CH₂O | 2,5-dihydro-3-pyrrolyl |
| 840 | C≡C—CH₂O | 3-isoxazolyl |
| 841 | C≡C—CH₂O | 4-methyl-3-isoxazolyl |
| 842 | C≡C—CH₂O | 5-methyl-3-isoxazolyl |
| 843 | C≡C—CH₂O | 4,5-dimethyl-3-isoxazolyl |
| 844 | C≡C—CH₂O | 4,5-dihydro-3-isoxazolyl |
| 845 | C≡C—CH₂O | 4-methyl-4,5-dihydro-3-isoxazolyl |
| 846 | C≡C—CH₂O | 5-methyl-4,5-dihydro-3-isoxazolyl |
| 847 | C≡C—CH₂O | 4,5-dimethyl-4,5-dihydro-3-isoxazolyl |
| 848 | C≡C—CH₂O | 4-isoxazolyl |
| 849 | C≡C—CH₂O | 3-methyl-4-isoxazolyl |
| 850 | C≡C—CH₂O | 5-methyl-4-isoxazolyl |
| 851 | C≡C—CH₂O | 5-cyclopropyl-4-isoxazolyl |
| 852 | C≡C—CH₂O | 5-phenyl-4-isoxazolyl |
| 853 | C≡C—CH₂O | 3,5-dimethyl-4-isoxazolyl |
| 854 | C≡C—CH₂O | 4,5-dihydro-4-isoxazolyl |
| 855 | C≡C—CH₂O | 3-methyl-4,5-dihydro-4-isoxazolyl |
| 856 | C≡C—CH₂O | 5-methyl-4,5-dihydro-4-isoxazolyl |
| 857 | C≡C—CH₂O | 3,5-dimethyl-4,5-dihydro-4-isoxazolyl |
| 858 | C≡C—CH₂O | 5-isoxazolyl |
| 859 | C≡C—CH₂O | 3-methyl-5-isoxazolyl |
| 860 | C≡C—CH₂O | 4-methyl-5-isoxazolyl |
| 861 | C≡C—CH₂O | 3,4-dimethyl-5-isoxazolyl |
| 862 | C≡C—CH₂O | 4,5-dihydro-5-isoxazolyl |
| 863 | C≡C—CH₂O | 3-methyl-4,5-dihydro-5-isoxazolyl |
| 864 | C≡C—CH₂O | 4-methyl-4,5-dihydro-5-isoxazolyl |
| 865 | C≡C—CH₂O | 3,4-dimethyl-4,5-dihydro-5-isoxazolyl |
| 866 | C≡C—CH₂O | 3-isothiazolyl |
| 867 | C≡C—CH₂O | 4-methyl-3-isothiazolyl |
| 868 | C≡C—CH₂O | 5-methyl-3-isothiazolyl |
| 869 | C≡C—CH₂O | 4-isothiazolyl |
| 870 | C≡C—CH₂O | 3-methyl-4-isothiazolyl |
| 871 | C≡C—CH₂O | 5-methyl-4-isothiazolyl |
| 872 | C≡C—CH₂O | 5-isothiazolyl |
| 873 | C≡C—CH₂O | 3-methyl-5-isothiazolyl |
| 874 | C≡C—CH₂O | 4-methyl-5-isothiazolyl |
| 875 | C≡C—CH₂O | 2-oxazolyl |
| 876 | C≡C—CH₂O | 4-oxazolyl |
| 877 | C≡C—CH₂O | 5-oxazolyl |
| 878 | C≡C—CH₂O | 2-thiazolyl |
| 879 | C≡C—CH₂O | 4-thiazolyl |
| 880 | C≡C—CH₂O | 5-thiazolyl |
| 881 | C≡C—CH₂O | 3-pyrazolyl |
| 882 | C≡C—CH₂O | 4-pyrazolyl |
| 883 | C≡C—CH₂O | 1-methyl-3-pyrazolyl |
| 884 | C≡C—CH₂O | 1-methyl-4-pyrazolyl |
| 885 | C≡C—CH₂O | 1-methyl-5-pyrazolyl |
| 886 | C≡C—CH₂O | 2-imidazolyl |
| 887 | C≡C—CH₂O | 1-methyl-2-imidazolyl |
| 888 | C≡C—CH₂O | 5-methyl-[1,3,4]-2-oxadiazolyl |
| 889 | C≡C—CH₂O | 5-methyl-[1,2,4]-3-oxadiazolyl |
| 890 | C≡C—CH₂O | 5-methyl-[1,3,4]-2-thiadiazolyl |
| 891 | C≡C—CH₂O | 5-methyl-[1,2,4]-3-thiadiazolyl |
| 892 | C≡C—CH₂O | [1,2,4]-3-triazolyl |
| 893 | C≡C—CH₂O | [1,2,3]-4-triazolyl |
| 894 | C≡C—CH₂O | 2-pyridyl |
| 895 | C≡C—CH₂O | 6-chloro-2-pyridyl |
| 896 | C≡C—CH₂O | 6-methoxy-2-pyridyl |
| 897 | C≡C—CH₂O | 6-trifluoromethyl-2-pyridyl |
| 898 | C≡C—CH₂O | 3-pyridyl |
| 899 | C≡C—CH₂O | 2-chloro-3-pyridyl |
| 900 | C≡C—CH₂O | 2-methoxy-3-pyridyl |
| 901 | C≡C—CH₂O | 4-pyridyl |
| 902 | C≡C—CH₂O | 2-chloro-4-pyridyl |
| 903 | C≡C—CH₂O | 2-methoxy-4-pyridyl |
| 904 | C≡C—CH₂O | 2-ethoxy-4-pyridyl |
| 905 | C≡C—CH₂O | 2-methylthio-4-pyridyl |
| 906 | C≡C—CH₂O | 2-trifluoromethyl-5-pyridyl |
| 907 | C≡C—CH₂O | 2-pyrimidinyl |
| 908 | C≡C—CH₂O | 3-pyrimidinyl |
| 909 | C≡C—CH₂O | 4-pyrimidinyl |
| 910 | C≡C—CH₂O | 2-pyrazinyl |
| 911 | C≡C—CH₂O | 3-pyridazinyl |
| 912 | C≡C—CH₂O | 4-pyridazinyl |
| 913 | C≡C—CH₂O | 2-(2H-1,3-oxazinyl) |
| 914 | C≡C—CH₂O | 2-(6H-1,3-oxazinyl) |
| 915 | C≡C—CH₂O | 4-(6H-1,3-oxazinyl) |
| 916 | C≡C—CH₂O | 6-(6H-1,3-oxazinyl) |
| 917 | C≡C—CH₂O | [1,3,5]-2-triazinyl |
| 918 | C≡C—CH₂O | [1,2,4]-3-triazinyl |
| 919 | C≡C—CH₂O | [1,2,4]-5-triazinyl |
| 920 | C≡C—CH₂O | [1,2,4]-6-triazinyl |

*The bridge X¹ is connectect at the left end with the central phenyl radical and at the right end with Het.

The Tables 1–36 below are based on the 2-benzoylcyclohexane-1,3-diones of the formula Ib:

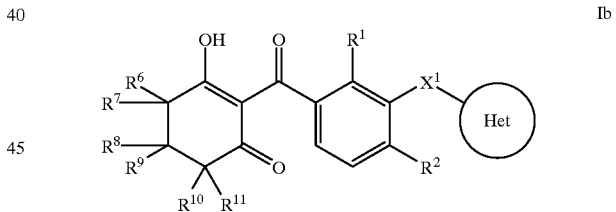

Ib

Table 1: Compounds 1.1–1.920
Compounds of the formula Ib, where R¹ is chlorine, R² is methylsulfonyl, R⁶, R⁷, R⁸, R⁹, R¹⁰ and R¹¹ are each hydrogen and where for each individual compound the substituents X¹ and Het correspond to one line of Table A.

Table 2: Compounds 2.1–2.920
Compounds of the formula Ib, where R¹ and R² are each chlorine, R⁶, R⁷, R⁸, R⁹, R¹⁰ and R¹¹ are each hydrogen and where for each individual compounds the substituents X¹ and Het corresponds to one line of Table A.

Table 3: Compounds 3.1–3.920
Compounds of the formula Ib, where R¹ is chlorine, R² is trifluoromethyl, R⁶, R⁷, R⁸, R⁹, R¹⁰ and R¹¹ are each hydrogen and where for each individual compound the substituents X¹ and Het correspond to one line of Table A.

Table 4: Compounds 4.1–4.920
Compounds of the formula Ib, where R¹ is methyl, R² is chlorine, R⁶, R⁷, R⁸, R⁹, R¹⁰ and R¹¹ are each hydrogen and where for each individual compound the substituents X¹ and Het correspond to one line of Table A.

Table 5: Compounds 5.1–5.920
Compounds of the formula Ib, where $R^1$ is methyl, $R^2$ is methylsulfonyl, $R^6$, $R^7$, $R^8$, $R^9$, $R^{10}$ and $R^{11}$ are each hydrogen and where for each individual compound the substituents $X^1$ and Het correspond to one line of Table A.

Table 6: Compounds 6.1–6.920
Compounds of the formula Ib, where $R^1$ is methyl, $R^2$ is trifluoromethyl, $R^6$, $R^7$, $R^8$, $R^9$, $R^{10}$ and $R^{11}$ are each hydrogen and where for each individual compound the substituents $X^1$ and Het correspond to one line of Table A.

Table 7: Compounds 7.1–7.920
Compounds of the formula Ib, where $R^1$ is chlorine, $R^2$ is methylsulfonyl, $R^6$, $R^7$, $R^{10}$ and $R^{11}$ are each hydrogen, $R^8$ and $R^9$ are each methyl and where for each individual compound the substituents $X^1$ and Het correspond to one line of Table A.

Table 8: Compounds 8.1–8.920
Compounds of the formula Ib, where $R^1$ and $R^2$ are each chlorine, $R^6$, $R^7$, $R^{10}$ and $R^{11}$ are each hydrogen, $R^8$ and $R^9$ are each methyl and where for each individual compound the substituents $X^1$ and Het correspond to one line of Table A.

Table 9: Compounds 9.1–9.920
Compounds of the formula Ib, where $R^1$ is chlorine, $R^2$ is trifluoromethyl, $R^6$ $R^7$, $R^{10}$ and $R^{11}$ are each hydrogen, $R^8$ and $R^9$ are each methyl and where for each individual compound the substituents $X^1$ and Het correspond to one line of Table A.

Table 10: Compounds 10.1–10.920
Compounds of the formula Ib, where $R^1$ is methyl, $R^2$ is chlorine, $R^6$, $R^7$, $R^{10}$ and $R^{11}$ are each hydrogen, $R^8$ and $R^9$ are each methyl and where for each individual compound the substituents $X^1$ and Het correspond to one line of Table A.

Table 11: Compounds 11.1–11.920
Compounds of the formula Ib, where $R^1$ is methyl, $R^2$ is methylsulfonyl, $R^6$, $R^7$, $R^{10}$ and $R^{11}$ are each hydrogen, $R^8$ and $R^9$ are each methyl and where for each individual compound the substituents $X^1$ and Het correspond to one line of Table A.

Table 12: Compounds 12.1–12.920
Compounds of the formula Ib, where $R^1$ is methyl, $R^2$ is trifluoromethyl, $R^6$, $R^7$, $R^{10}$ and $R^{11}$ are each hydrogen, $R^8$ and $R^9$ is methyl and where for each individual compound the substituents $X^1$ and Het correspond to one line of Table A.

Table 13: Compounds 13.1–13.920
Compounds of the formula Ib, where $R^1$ is chlorine, $R^2$ is methylsulfonyl, $R^6$, $R^7$, $R^8$ and $R^9$ are each hydrogen, $R^{10}$ and $R^{11}$ are each methyl and where for each individual compound the substituents $X^1$ and Het correspond to one line of Table A.

Table 14: Compounds 14.1–14.920
Compounds of the formula Ib, where $R^1$ and R2 is chlorine, $R^6$, $R^7$, $R^8$ and $R^9$ are each hydrogen, $R^{10}$ and $R^{11}$ are each methyl and where for each individual compound the substituents $X^1$ and Het correspond to one line of Table A.

Table 15: Compounds 15.1–15.920
Compounds of the formula Ib, where $R^1$ is chlorine, $R^2$ is trifluoromethyl, $R^6$, $R^7$, $R^8$ and $R^9$ are each hydrogen, $R^{10}$ and $R^{11}$ are each methyl and where for each individual compound the substituents $X^1$ and Het correspond to one line of Table A.

Table 16: Compounds 16.1–16.920
Compounds of the formula Ib, where $R^1$ is methyl, $R^2$ is chlorine, $R^6$, $R^7$, $R^8$ and $R^9$ are each hydrogen, $R^{10}$ and $R^{11}$ are each methyl and where for each individual compound the substituents $X^1$ and Het correspond to one line of Table A.

Table 17: Compounds 17.1–17.920
Compounds of the formula Ib, where $R^1$ is methyl, $R^2$ is methylsulfonyl, $R^6$, $R^7$, $R^8$ and $R^9$ are each hydrogen, $R^{10}$ and $R^{11}$ are each methyl and where for each individual compound the substituents $X^1$ and Het correspond to one line of Table A.

Table 18: Compounds 18.1–18.920
Compounds of the formula Ib, where $R^1$ is methyl, $R^2$ is trifluoromethyl, $R^6$, $R^7$, $R^8$ and $R^9$ are each hydrogen, $R^{10}$ and $R^{11}$ are each methyl and where for each individual compound the substituents $X^1$ and Het correspond to one line of Table A.

Table 19: Compounds 19.1–19.920
Compounds of the formula Ib, where $R^1$ is chlorine, $R^2$ is methylsulfonyl, $R^6$, $R^7$, $R^{10}$ and $R^{11}$ are each methyl, the $CR^8R^9$ unit forms a group C=O and where for each individual compound the substituents $X^1$ and Het correspond to one line of Table A.

Table 20: Compounds 20.1–20.920
Compounds of the formula Ib, where $R^1$ and $R^2$ are each chlorine, $R^6$, $R^7$, $R^{10}$ and $R^{11}$ are each methyl, the $CR^8R^9$ unit forms a group C=O and where for each individual compound the substituents $X^1$ and Het correspond to one line of Table A.

Table 21: Compounds 21.1–21.920
Compounds of the formula Ib, where $R^1$ is chlorine, $R^2$ is trifluoromethyl, $R^6$, $R^7$, $R^{10}$ and $R^{11}$ are each methyl, the $CR^8R^9$ unit forms a group C=O and where for each individual compound the substituents $X^1$ and Het correspond to one line of Table A.

Table 22: Compounds 22.1–22.920
Compounds of the formula Ib, where $R^1$ is methyl, $R^2$ is chlorine, $R^6$, $R^7$, $R^{10}$ and $R^{11}$ are each methyl, the $CR^8R^9$ unit forms a group C=O and where for each individual compound the substituents $X^1$ and Het correspond to one line of Table A.

Table 23: Compounds 23.1–23.920
Compounds of the formula Ib, where $R^1$ is methyl, $R^2$ is methylsulfonyl, $R^6$, $R^7$, $R^{10}$ and $R^{11}$ are each methyl, the $CR^8R^9$ unit forms a group C=O and where for each individual compound the substituents $X^1$ and Het correspond to one line of Table A.

Table 24: Compounds 24.1–24.920
Compounds of the formula Ib, where $R^1$ is methyl, $R^2$ is trifluoromethyl, $R^6$, $R^7$, $R^{10}$ and $R^{11}$ are each methyl, the $CR^8R^9$ unit forms a group C=O and where for each individual compound the substituents $X^1$ and Het correspond to one line of Table A.

Table 25: Compounds 25.1–25.920
Compounds of the formula Ib, where $R^1$ is methylsulfonyl, $R^6$, $R^7$, $R^8$, $R^{10}$ and $R^{11}$ are each hydrogen, $R^9$ is methyl, where for each individual compound the substituents $X^1$ and Het correspond to one line of Table A.

Table 26: Compounds 26.1–26.920
Compounds of the formula Ib, where $R^1$ and $R^2$ are each chlorine, $R^6$, $R^7$, $R^8$, $R^{10}$ and $R^{11}$ are each hydrogen, $R^9$ is methyl and where for each individual compound the substituents $X^1$ and Het correspond to one line of Table A.

Table 27: Compounds 27.1–27.920
Compounds of the formula Ib, where $R^1$ is chlorine, $R^2$ is trifluoromethyl, $R^6$, $R^7$, $R^8$, $R^{10}$ and $R^{11}$ are each hydrogen, $R^9$ is methyl and where for each individual compound the substituents $X^1$ and Het correspond to one line of Table A.

Table 28: Compounds 28.1–28.920

Compounds of the formula Ib, where $R^1$ is methyl, $R^2$ is chlorine, $R^6$, $R^7$, $R^8$, $R^{10}$ and $R^{11}$ are each hydrogen, $R^9$ is methyl and where for each individual compound the substituents $X^1$ and Het correspond to one line of Table A.
Table 29: Compounds 29.1–29.920

Compounds of the formula Ib, where $R^1$ is methyl, $R^2$ is methylsulfonyl, $R^6$, $R^7$, $R^8$, $R^{10}$ and $R^{11}$ are each hydrogen, $R^9$ is methyl and where for each individual compound the substituents $X^1$ and Het correspond to one line of Table A.
Table 30: Compounds 30.1–30.920

Compounds of the formula Ib, where $R^1$ is methyl, $R^2$ is trifluoromethyl, $R^6$, $R^7$, $R^8$, $R^{10}$ and $R^{11}$ are each hydrogen, $R^9$ is methyl and where for each individual compound the substituents $X^1$ and Het correspond to one line of Table A.
Table 31: Compounds 31.1–31.920

Compounds of the formula Ib, where $R^1$ is chlorine, $R^2$ is methylsulfonyl, $R^6$, $R^7$, $R^9$ and $R^{10}$ are each hydrogen, $R^8$ and $R^{11}$ together form a methylene group and where for each individual compound the substituents $X^1$ and Het correspond to one line of Table A.
Table 32: Compounds 32.1–32.920

Compounds of the formula Ib, where $R^1$ and $R^2$ are each chlorine, $R^6$, $R^7$, $R^9$ and $R^{10}$ are each hydrogen, $R^8$ and $R^{11}$ together form a methylene group and where for each individual compound the substituents $X^1$ and Het correspond to one line of Table A.
Table 33: Compounds 33.1–33.920

Compounds of the formula Ib, where $R^1$ is chlorine, $R^2$ is trifluoromethyl, $R^6$, $R^7$, $R^9$ and $R^{10}$ are each hydrogen, $R^8$ and $R^{11}$ together form a methylene group and where for each individual compound the substituents $X^1$ and Het correspond to one line of Table A.
Table 34: Compounds 34.1–34.920

Compounds of the formula Ib, where $R^1$ is methyl, $R^2$ is chlorine, $R^6$, $R^7$, $R^9$ and $R^{10}$ are each hydrogen, $R^8$ and $R^{11}$ together form a methylene group and where for each individual compound the substituents $X^1$ and Het correspond to one line of Table A.
Table 35: Compounds 35.1–35.920

Compounds of the formula Ib, where $R^1$ is methyl, $R^2$ is methylsulfonyl, $R^6$, $R^7$, $R^9$ and $R^{10}$ are each hydrogen, $R^8$ and $R^{11}$ together form a methylene group and where for each individual compound the substituents $X^1$ and Het correspond to one line of Table A.
Table 36: Compounds 36.1–36.920

Compounds of the formula Ib, where $R^1$ is methyl, $R^2$ is trifluoromethyl, $R^6$, $R^7$, $R^9$ and $R^{10}$ are each hydrogen, $R^8$ and $R^{11}$ together form a methylene group and where for each individual compound the substituents $X^1$ and Het correspond to one line of Table A.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broadleaved weeds and grass weeds in crops such as wheat, rice, maize, soya and cotton without causing any significant damage to the crop plants. This effect is mainly observed at low rates of application.

Depending on the application method used, the compounds I, or the compositions comprising them, can additionally be employed in a further number of crop plants for eliminating unwanted plants.

Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus avium, Prunus persica, Pyrus communnis, Ribes sylvestre, Ricinus communis, Saccharum officinarum, Secale cereale, Solanum tuberosum, Sorghum bicolor* (*S. vulgare*), *Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The herbicidal compositions or the active compounds can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of unwanted plants growing underneath, or the bare soil surface (post-directed, lay-by).

The compounds I, or the herbicidal compositions comprising them, can be used for example in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, broadcasting or watering. The application forms depend on the intended uses; in any case, they should guarantee a very fine distribution of the active compounds according to the invention.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substituted 2-benzoylcyclohexane-1,3-diones, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the active compounds together with a solid carrier.

Granules, eg. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to the NMR spectrum).

The compounds I according to the invention can be formulated for example as follows:

I 20 parts by weight of the compound I are dissolved in a mixture composed of 80 parts by weight of alkylated benzene, 10 parts by weight of the adduct of 8 to 10 mol of ethylene oxide with 1 mol of oleic acid N-monoethanolamide, 5 parts by weight of calcium dodecylbenzenesulfonate and 5 parts by weight of the adduct of 40 mol of ethylene oxide with 1 mol of castor oil. Pouring the solution into 100,000 parts by weight of water and finely distributing it therein gives an aqueous dispersion which comprises 0.02% by weight of the active compound.

II 20 parts by weight of the compound I are dissolved in a mixture composed of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. Pouring the solution into 100,000 parts by weight of water and finely distributing it therein gives an aqueous dispersion which comprises 0.02% by weight of the active compound.

III 20 parts by weight of the compound I are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide with 1 mol of castor oil. Pouring the solution into 100,000 parts by weight of water and finely distributing it therein gives an aqueous dispersion which comprises 0.02% by weight of the active compound.

IV 20 parts by weight of the compound I are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V 3 parts by weight of the compound I are mixed with 97 parts by weight of finely divided kaolin. This gives a dust which comprises 3% by weight of the active compound.

VI 20 parts by weight of the compound I are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of the compound I is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the compound I is dissolved in a mixture composed of 80 parts by weight of cyclohexanone and 20 parts by weight of Wettol® EM 31 (nonionic emulsifier based on ethoxylated castor oil). This gives a stable emulsion concentrate.

To widen the activity spectrum and to achieve synergistic effects, the substituted 2-benzoylcyclohexane-1,3-diones I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, bipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The active compound application rates are from 0.001 to 3.0, preferably 0.01 to 1.0 kg/ha of active substance (a.s.), depending on the control target, the season, the target plants and the growth stage.

The syntheses of some starting materials and products are described below.

{2-chloro-3-[(1-methylpyrazol-5-yl)oxymethyl]-4-methyl-sulfonylphenyl}{5,5-dimethyl-1,3-dioxo-cyclohex-2-yl}methanone step a: methyl 2-chloro-3-bromomethyl-4-methylsulfonylbenzoate 80 g (0.3 mol) of methyl 2-chloro-3-methyl-4-methylsulfonylbenzoate, 54 g (0.31 mol) of N-bromosuccinimide and 1.5 g of azoisobutyronitrile are stirred at 76° C. for 6 h. The reaction mixture is filtered and freed form the solvent under reduced pressure. Yield: 104 g; m.p. 83–85° C.

step b: methyl 2-chloro-[(1-methylpyrazol-5-yl)oxymethyl]-4-methylsulfonylbenzoate 4.3 g (44 mmol) of 1-methyl-5-hydroxypyrazol, 9.1 g of potassium carbonate and 100 ml of tetrahydrofurane are heated at 65° C. for 1 h. 15 g (44 mmol) of methyl 2-chloro-3-bromomethyl-4-methylsulfonylbenzoate and 150 ml of tetrahydrofurane are added to this mixture and heated at 40° C. for 4 h. This mixture is stirred for 12 h, freed from the solvent under reduced pressure, taken up in ethyl acetate, washed with sodium bicarbonate solution and water, dried and freed form the solvent. The crude product is purified over silica gel (eluent: cyclohexane/ethyl acetate= 1/1). Yield: 7.6 g; m.p. 70° C.

Step c: 2-chloro-[(1-methylpyrazol-5-yl)oxymethyl]-4-methylsulfonyl benzoic acid 6.95 g (19 mmol) of methyl 2-chloro-[(1-methylpyrazol-5-yl)oxymethyl]-4-methylsulfonylbenzoate in a mixture of 30 ml of tetrahydrofurane and 30 ml of water are treated at room temperature with 0.93 g of lithium hydroxide for 12 h. The reaction mixture is adjusted to pH4 with 10% strength hydrochloric acid and extracted with methylene chloride. The organic phase is dried and freed from the solvent. Yield: 4.3 g; m.p. 197° C.

Step d: {2-chloro-3-[(1-methylpyrazol-5-yl)oxymethyl]-4-methylsulfonylphenyl}{5,5-dimethyl-1,3-dioxo-cyclohex-2-yl}methanone 1.0 g (2.9 mmol) of 2-chloro-3-[(1-methylpyrazol-5-yl)oxymethyl]-4-methylsulfonyl benzoic acid, 0.4 g (2.9 mmol) of dimedone and 0.72 g of N,N-dicyclohexylcarbodiimide in 50 ml of acetonitrile are heated at 40° C. for 4 h. After the reaction mixture has been stirred for 12 h at room temperature, 0.87 g of triethylamine and 0.57 g of trimethylsilylnitrile are added. Afterwards the reaction mixture is heated at 40° C. for 6 h, filtered, freed from the solvent under reduced pressure and the residue is purified over silica gel (eluent: toluene/tetrahydrofurane/acetic acid: 100/0/0→4/1/0.1). Yield: 0.25 g; m.p.82° C.

TABLE 37

| No. | $R^6$ | $R^7$ | $R^8$ | $R^9$ | $R^{10}$ | $R^{11}$ | $X^1$ | Het | M.p. [° C.] | $^1$H NMR [ppm] |
|---|---|---|---|---|---|---|---|---|---|---|
| 37.1 | H | H | $CH_3$ | $CH_3$ | H | H | $CH_2O$ | 1-methylpyrazal-5-yl | 82 | |
| 37.2 | H | H | $CH_3$ | $CH_3$ | H | H | $CH_2O$ | 3,5-dimethyl-1-pyrazolyl | 76 | |
| 37.3 | H | H | $CH_3$ | $CH_3$ | H | H | $CH_2O$ | 4-chloro-1-pyrazolyl | 75 | |
| 37.4 | H | $CH_3$ | H | H | H | $CH_3$ | $CH_2O$ | 3,5-dimethyl-1-pyrazolyl | 74 | |
| 37.5 | H | $CH_3$ | H | H | H | $CH_3$ | $CH_2O$ | 4-chloro-1-pyrazolyl | 79 | |
| 37.6 | $CH_3$ | $CH_3$ | C=O | | $CH_3$ | $CH_3$ | $CH_2O$ | 3,5-dimethyl-1-pyrazolyl | 137 | |
| 37.7 | $CH_3$ | $CH_3$ | C=O | | $CH_3$ | $CH_3$ | $CH_2O$ | 4-chloro-1-pyrazolyl | 95 | |

USE EXAMPLES

The herbicidal activity of the substituted 2-benzoylcyclohexane-1,3-diones of the formula I was demonstrated by greenhouse experiments:

The culture containers used were plastic pots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants, unless this was adversely affected by the active compounds.

For the post-emergence treatment, the test plants were first grown to a height of 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment.

Depending on the species, the plants were kept at 10–25° C. or 20–35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the above-ground parts, and 0 means no damage, or normal course of growth.

We claim:

1. A 2-benzoylcyclohexane-1,3-dione of formula I:

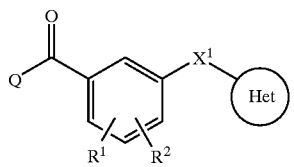

where:

$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl, —$OR^3$, —$OCOR^3$, —$OSO_2R^3$, —$S(O)_nR^3$, —$SO_2OR^3$, —$SO_2N(R^3)_2$, —$NR^3SO_2R^3$ or —$NR^3COR^3$;

$R^3$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl; where the abovementioned alkyl radicals may be partially or fully halogenated and/or may carry one to three of the following groups: hydroxyl, mercapto, amino, cyano;

n is 0, 1 or 2;

Q is a cyclohexane-1,3-dione ring with or without substitution which is attached in position 2;

$X^1$ is a straight-chain or branched $C_1$–$C_6$-alkylene, a $C_2$–$C_6$-alkenylene or a $C_2$–$C_6$-alkynylene chain which is interrupted by a hetero atom selected from the group consisting of: oxygen or sulfur, where the abovementioned alkyl, alkenyl or alkynyl radicals may be partially halogenated and/or may carry one to three of the following groups: —$OR^4$, —$OCOR^4$, —$OCONHR^4$ or —$OSO_2R^4$;

$R^4$ is hydrogen, $C_1$–$C_6$-alkyl, $C_2$–$C_6$-alkenyl, $C_2$–$C_6$-alkynyl, phenyl, phenyl-$C_1$–$C_6$-alkyl, where the abovementioned alkyl, alkenyl or alkynyl radicals may be partially or fully halogenated and/or may be substituted by one or more of the following radicals:

hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

Het is a three- to six-membered partially or fully saturated heterocyclic group or a three- to six-membered heteroaromatic group having up to three nitrogen ring members as hetero atoms, where the abovementioned heterocyclic or heteroaromatic group may be partially or fully halogenated and/or may be substituted by $R^5$;

$R^5$ is hydrogen, hydroxyl, mercapto, amino, cyano, nitro, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy, where the alkyl radicals may in each case be substituted by in each case one or more of the following radicals:

cyano, formyl, $C_1$–$C_4$-alkylamino, $C_1$–$C_4$-dialkylamino, $C_1$–$C_4$-alkoxycarbonyl, $C_1$–$C_4$-alkylcarbonyl, $C_1$–$C_4$-alkylcarbonyloxy, $C_1$–$C_4$-alkyl, $C_1$–$C_4$-haloalkyl, $C_1$–$C_4$-alkylthio, $C_1$–$C_4$-haloalkylthio, $C_1$–$C_4$-alkoxy, $C_1$–$C_4$-haloalkoxy;

or an agriculturally useful salt thereof.

2. The 2-benzoylcyclohexane-1,3-dione of formula I defined in claim 1 wherein the cyclohexane-1,3-dione ring Q is of formula II

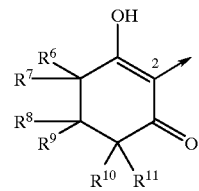

wherein $R^6$, $R^7$, $R^9$ and $R^{11}$ are each hydrogen or $C_1$–$C_4$-alkyl;

$R^8$ is hydrogen, $C_1$–$C_4$-alkyl or $C_3$–$C_4$-cycloalkyl, where the two last mentioned groups may carry one to three of the following substituents: halogen, $C_1$–$C_4$-alkylthio or $C_1$–$C_4$-alkoxy; or is tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the 6 last mentioned radicals may be substituted by one to three $C_1$–$C_4$-alkyl radicals;

$R^{10}$ is hydrogen, $C_1$–$C_4$-alkyl or $C_1$–$C_6$-alkoxycarbonyl; or $R^8$ and $R^{11}$ together form π bond or a three- to six-membered carbocyclic ring; or the $CR^8R^9$ unit represents a C=O group.

3. The 2-benzoylcyclohexane-1,3-dione of formula I defined in claim 1, wherein $R^1$ is nitro, halogen, cyano, thiocyanato, $C_1$–$C_6$-alkyl, $C_1$–$C_6$-haloalkyl, $C_1$–$C_6$-alkoxy, $C_2$–$C_6$-alkenyl, $C_2$–$C_6$-alkynyl, —$OR^3$ or —$S(O)_nR^3$;

$R^2$ is hydrogen or one of the radicals mentioned above under $R^1$.

4. The 2-benzoylcyclohexane-1,3-dione defined in claim 1 which is of formula Ia:

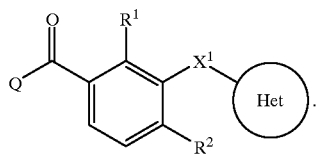

5. The 2-benzoylcyclohexane-1,3-dione of formula Ia defined in claim 4 wherein $X^1$ is a $C_1$–$C_3$-alkylene, $C_2$–$C_3$-alkenylene or $C_2$–$C_3$-alkynylene chain which is interrupted by an oxygen.

6. The 2-benzoylcyclohexane-1,3-dione of formula Ia defined in claim 4 wherein Het is a five- or six-membered partially or fully saturated heterocyclic or a 5- or 6-membered heteroaromatic group having up to three nitrogen ring members as hetero atoms.

7. The 2-benzoylcyclohexane-1,3-dione of formula I defined in claim 1, wherein $R^1$ is nitro, halogen, $C_1$–$C_6$-haloalkyl, —$OR^3$ or —$SO_2R^3$.

8. The 2-benzoylcyclohexane-1,3-dione of formula I defined in claim 1, wherein $R^2$ is hydrogen, nitro, halogen, $C_1$–$C_6$-alkyl, $C_1$–$C_6$-haloalkyl, —$OR^3$ or —$SO_2R^3$.

9. The 2-benzoylcyclohexane-1,3-dione of formula I defined in claim 1, wherein $R^3$ is hydrogen, $C_1$–$C_4$-alkyl, $C_1$–$C_4$-haloalkyl, $C_2$–$C_3$-alkenyl, $C_2$–$C_3$-alkynyl or phenyl, wherein the alkyl radicals may be partially or fully halogenated and/or may carry one to three of the following groups: hydroxyl, mercapto, amino, cyano.

10. The 2-benzoylcyclohexane-1,3-dione of formula I defined in claim 1, wherein n is 0 or 2.

11. The 2-benzoylcyclohexane-1,3-dione of formula I defined in claim 1, wherein $X^1$ is a straight-chain or branched $C_1$–$C_4$-alkylene, a $C_2$–$C_4$-alkenylene or a $C_2$–$C_4$-alkynylene chain which is interrupted by a hetero atom selected from the group consisting of oxygen and sulfur, and wherein the alkylene, alkenylene or alkynylene radicals may be partially halogenated and/or may carry one to three of the following groups: —$OR^4$, —$OCOR^4$, —$OCONHR^4$ or —$OSO_2R^4$.

12. The 2-benzoylcyclohexane-1,3-dione defined in claim 11, wherein $X^1$ is ethylene, propylene, propenylene or propynylene chain which is interrupted by an oxygen atom.

13. The 2-benzoylcyclohexane-1,3-dione of formula I defined in claim 1, wherein $R^4$ is hydrogen, $C_1$–$C_6$-alkyl or $C_1$–$C_6$-haloalkyl.

14. The 2-benzoylcyclohexane-1,3-dione of formula I defined in claim 1 wherein Het is a five- or six-membered partially or fully saturated heterocyclic or a 5- or 6-membered heteroaromatic group having up to three nitrogen ring members as hetero atoms.

15. The 2-benzoylcyclohexane-1,3-dione of formula I defined in claim 2 wherein Het is a five- or six-membered partially or fully saturated heterocyclic or a 5- or 6-membered heteroaromatic group having up to three nitrogen ring members as hetero atoms.

16. A process for preparing the 2-benzoylcyclohexane-1,3-dione of formula I defined in claim 1, which comprises acylating a substituted or unsubstituted cyclohexane-1,3-dione Q with an activated carboxylic acid IIIa or with a carboxylic acid IIIb,

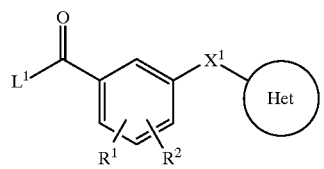

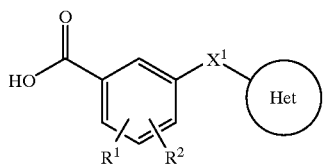

wherein $L^1$ is a nucleophilically replaceable leaving group, and rearranging the acylation product, optionally in the presence of a catalyst, to a compound I.

17. An activated carboxylic acid of formula IIIa or a carboxylic acid of formula IIIb as defined in claim 16.

18. A composition comprising a herbicidally effective amount of at least one 2-benzoylcyclohexane-1,3-dione of formula I defined in claim 1 or an agriculturally useful salt of I and auxiliaries which are customarily used for formulating crop protection agents.

19. A process for preparing the composition defined in claim 18, which comprises mixing a herbicidally effective amount of at least one 2-benzoylcyclohexane-1,3-dione of formula I or an agriculturally useful salt of I and auxiliaries which are customarily used for formulating crop protection agents.

20. A method for controlling unwanted vegetation, which comprises allowing a herbicidally effective amount of at least one 2-benzoylcyclohexane-1,3-dione of formula I defined in claim 1 or an agriculturally useful salt of I to act on plants, their habitat and/or on seeds.

* * * * *